US007070977B2

(12) United States Patent
Darrow et al.

(10) Patent No.: US 7,070,977 B2
(45) Date of Patent: Jul. 4, 2006

(54) HUMAN SERINE PROTEASE D-G POLYPEPTIDE

(75) Inventors: Andrew L. Darrow, Lansdale, PA (US); Jenson (Jian-Shen) Qi, Branchburg, NJ (US); Patricia Andrade-Gordon, Doylestown, PA (US)

(73) Assignee: Ortho-McNeil Pharmaceutical, Inc., Rarrtan, NJ (US)

( * ) Notice: Subject to any disclaimer, the term of this patent is extended or adjusted under 35 U.S.C. 154(b) by 160 days.

(21) Appl. No.: 10/803,530

(22) Filed: Mar. 17, 2004

(65) Prior Publication Data

US 2004/0146981 A1    Jul. 29, 2004

Related U.S. Application Data

(62) Division of application No. 09/607,745, filed on Jun. 30, 2000, now Pat. No. 6,750,034.

(51) Int. Cl.
   C12N 9/64    (2006.01)
   C12P 21/06   (2006.01)
   C07K 1/00    (2006.01)

(52) U.S. Cl. ...................... 435/226; 435/69.1; 530/412
(58) Field of Classification Search ...................... None
    See application file for complete search history.

(56) References Cited

U.S. PATENT DOCUMENTS

| 5,200,340 A | 4/1993 | Foster et al. |
| 5,665,566 A | 9/1997 | La Vallie |
| 6,203,979 B1 | 3/2001 | Bandman et al. |
| 2003/0166162 A1 | 9/2003 | Van Rooijen et al. |

FOREIGN PATENT DOCUMENTS

| WO | WO 9747737 | 12/1997 |
| WO | WO 9849326 | 11/1998 |
| WO | WO 9936550 | 7/1999 |
| WO | WO 0012708 | 3/2000 |
| WO | WO 0104141 | 1/2001 |
| WO | WO 0116289 | 3/2001 |
| WO | WO 0157194 | 8/2001 |

OTHER PUBLICATIONS

Vuagniaux et al., Synergistic activation of ENaC by three membrane-bound channel-activating serine proteases (mCAP1, mCAP2, and mCAP3) and serum- and glucocorticoid-regulated kinase (Sgk1) in Xenopus Oocytes. J Gen Physiol. Aug. 2002;120(2): 191-201.*
UniProt Database Accession No. TMPS4_MOUSE Oct. 10, 2003 from Vuagniaux et al., Synergistic activation of ENaC by three membrane-bound channel-activating serine proteases (mCAP1, mCAP2, and mCAP3) . . . Gen Physiol. Aug. 2002;120(2):1. Alignment with SEQ ID No. 2.*
UniProt Database Accession No. TMPS4_HUMAN Oct. 16, 2001 from Wallrapp et al., A novel transmembrane serine protease (TMPRSS3) overexpressed in pancreatic cancer. Cancer Res. May 15, 2000;60(10):2602-6. Alignment with SEQ ID No. 2.*
U. S. Appl. No. filed Jan. 16, 1998 6,203,979, Bandman et al. SEQ ID No: 6. Alignment wutg SEQ ID No:2.*
Database EMBL Accession No. AAX87154, Bandman et al., "Novel Human Protease Molecules Useful In The Treatment Of Developmental Disorders And/Or Cancers" (1999).
Database EMBL Accession No. AAY06437, Bandman et al., "Novel Human Protease Molecules Useful In The Treatment Of Developmental Disorders And/Or Cancers" (1999).
Database GENSEQ Accession No. AAY99417, Baker et al., "New Mammalian DNA Sequences Encoding Transmembrane, Receptor Or Secreted PRO Polypeptides, Useful For Screening Of Potential Peptide Or Small Molecule Inhibitors Of The Relevant Receptor/Ligand Interactions" (2000).
Database GENEMBL Accession No. AF179224, Wallrapp et al., "A Novel Transmembrane Serine Protease (TMPRSS3) Overexpressed In Pancreatic Cancer" (2000).
Database GENEMBL Accession No. AF216312, Smeekens et al., "MT-SP2, A Novel Type II Membrane Serine Protease Expressed In Trachea, Colon and Small Intestine: Identification, Cloning, And Chromosomal Localization" (2000).
Davie et al., "The Coagulation Cascade: Initiation, Maintenance, And Regulation," *Biochemistry*, vol. 30(43), pp. 10363-10370 (1991).
Ishii et al., "Kinetics Of Thrombin Receptor Cleavage On Intact Cells," *J. Biol. Chem.*, vol. 268(13), pp. 9780-9786 (1993).
Kuhn et al., "The Baculovirus Expression Vector pBSV-8His Directs Secretion Of Histidine-Tagged Proteins," *Gene*, vol. 162, pp. 225-229 (1995).
Leytus et al., "A Novel Trypsin-like Serine Protease (Hepsin) With A Putative Transmembrane Domain Expressed By Human Liver And Hepatoma Cells," *Biochemsitry*, vol. 27, pp. 1067-1074 (1988).
Paoloni-Giacobino et al., "Cloning Of The TMPRSS2 Gene, Which Encodes A Novel Serine Protease With Transmembrane, LDLRA, And SRCR Domains And Maps To 21q22.3," *Genomics*, vol. 44, pp. 309-320 (1997).
Proud et al., "Kinin Formation: Mechanisms And Role In Inflammatory Disorders," *Annu. Rev. Immunol.*, vol. 6, pp. 49-83 (1988).
Reid et al., "The Proteolytic Activation Systems Of Complement," *Ann. Rev. Biochem.*, vol. 50, pp. 433-464 (1981).

* cited by examiner

*Primary Examiner*—Sheridan Swope

(57) ABSTRACT

Polypeptides corresponding to a novel S1 serine protease family member, termed protease D-G, and nucleic acids encoding them are described. The materials may be used, for example, in screening assays to identify protease D-G modulators and in methods for diagnosing or treating conditions associated with aberrant protease D-G activity.

1 Claim, 8 Drawing Sheets

FIGURE 1 A

NUCLEOTIDE SEQUENCE

>protease D-G (SEQ.ID.NO.:1)

CAACTTCACTTGTAGGGCTGTTTTAATCAAGCTGCCCAAAGTCCCCCAATCACTCCTGGA
ATACACAGAGAGAGGCAGCAGCTTGCTCAGCGGACAAGGATGCTGGGCGTGAGGGACCAA
GGCCTGCCCTGCACTCGGGCCTCCTCCAGCCAGTGCTGACCAGGGACTTCTGACCTGCTG
GCCAGCCAGGACCTGTGTGGGGAGGCCCTCCTGCTGCCTTGGGGTGACAATCTCAGCTCC
AGGCTACAGGGAGACCGGGAGGATCACAGAGCCAGCATGGATCCTGACAGTGATCAACCT
CTGAACAGCCTCGATGTCAAACCCCTGCGCAAACCCCGTATCCCCATGGAGACCTTCAGA
AAGGTGGGGATCCCCATCATCATAGCACTACTGAGCCTGGCGAGTATCATCATTGTGGTT
GTCCTCATCAAGGTGATTCTGGATAAATACTACTTCCTCTGCGGGCAGCCTCTCCACTTC
ATCCCGAGGAAGCAGCTGTGTGACGGAGAGCTGGACTGTCCCTTGGGGGAGGACGAGGAG
CACTGTGTCAAGAGCTTCCCCGAAGGGCCTGCAGTGGCAGTCCGCCTCTCCAAGGACCGA
TCCACACTGCAGGTGCTGGACTCGGCCACAGGGAACTGGTTCTCTGCCTGTTTCGACAAC
TTCACAGAAGCTCTCGCTGAGACAGCCTGTAGGCAGATGGGCTACAGCAGCAAACCCACT
TTCAGAGCTGTGGAGATTGGCCCAGACCAGGATCTGGATGTTGTTGAAATCACAGAAAAC
AGCCAGGAGCTTCGCATGCGGAACTCAAGTGGGCCCTGTCTCTCAGGCTCCCTGGTCTCC
CTGCACTGTCTTGCCTGTGGGAAGAGCCTGAAGACCCCCGTGTGGTGGGTGGGGAGGAG
GCCTCTGTGGATTCTTGGCCTTGGCAGGTCAGCATCCAGTACGACAAACAGCACGTCTGT
GGAGGGAGCATCCTGGACCCCCACTGGGTCCTCACGGCAGCCCACTGCTTCAGGAAACAT
ACCGATGTGTTCAACTGGAAGGTGCGGGCAGGCTCAGACAAACTGGGCAGCTTCCCATCC
CTGGCTGTGGCCAAGATCATCATCATTGAATTCAACCCCATGTACCCCAAAGACAATGAC
ATCGCCCTCATGAAGCTGCAGTTCCCACTCACTTTCTCAGGCACAGTCAGGCCCATCTGT
CTGCCCTTCTTTGATGAGGAGCTCACTCCAGCCACCCCACTCTGGATCATTGGATGGGGC
TTTACGAAGCAGAATGGAGGGAAGATGTCTGACATACTGCTGCAGGCGTCAGTCCAGGTC
ATTGACAGCACACGGTGCAATGCAGACGATGCGTACCTGGGGGAAGTCACCGAGAAGATG
ATGTGTGCAGGCATCCCGGAAGGGGGTGTGGACACCTGCCAGGGTGACAGTGGTGGGCCC
CTGATGTACCAATCTGACCAGTGGCATGTGGTGGGCATCGTTAGCTGGGGCTATGGCTGC
GGGGGCCCGAGCACCCCAGGGGTATACACCAAGGTCTCAGCCTATCTCAACTGGATCTAC
AATGTCTGGAAGGCTGAGCTGTAATGCTGCTGCCCCTTTGCAGTGCTGGGAGCCGCTTCC
TTCCTGCCCTGCCCACCTGGGGATCCCCCAAAGTCAGACACAGAGCAAGAGTCCCCTTGG
GTACACCCCTCTGCCCACAGCCTCAGCATTTCTTGGAGCAGCAAAGGGCCTCAATTCCTA
TAAGAGACCCTCGCAGCCCAGAGGCGCCCAGAGGAAGTCAGCAGCCCTAGCTCGGCCACA
CTTGGTGCTCCCAGCATCCCAGGGAGAGACACAGCCCACTGAACAAGGTCTCAGGGGTAT
TGCTAAGCCAAGAAGGAACTTTCCCACACTACTGAATGGAAGCAGGCTGTCTTGTAAAAG
CCCAGATCACTGTGGGCTGGAGAGGAGAAGGAAAGGGTCTGCGCCAGCCCTGTCCGTCTT
CACCCATCCCCAAGCCTACTAGAGCAAGAAACCAGTTGTAATATAAAATGCACTGCCTAC
TGTTGGTATGACTACCGTTACCTACTGTTGTCATTGTTATTACAGCTATGGCCACTATTA
TTAAAGAGCTGTGTAACATCA

FIGURE 1 B

AA SEQUENCE

>protease D-G (SEQ.ID.NO.:2)

MDPDSDQPLNSLDVKPLRKPRIPMETFRKV`GIPIIIALLSLASIIIVVVLIK`VILDKYYF
LCGQPLHFIPRKQLCDGELDCPLGEDEEHCVKSFPEGPAVAVRLSKDRSTLQVLDSATGN
WFSACFDNFTEALAETACRQMGYSSKPTFRAVEIGPDQDLDVVEITENSQELRMRNSSGP
CLSGSLVSLHCLACGKSLKTPR<u>VVGG</u>EEASVDSWPWQVSIQYDKQHVCGGSILDPHWVLT
AAHCFRKHTDVFNWKVRAGSDKLGSFPSLAVAKIIIEFNPMYPKDNDIALMKLQFPLTF
SGTVRPICLPFFDEELTPATPLWIIGWGFTKQNGGKMSDILLQASVQVIDSTRCNADDAY
QGEVTEKMMCAGIPEGGVDTCQGDSGGPLMYQSDQWHVVGIVSWGYGCGGPSTPGVYTKV
SAYLNWIYNVWKAEL

PHYLOGENETIC TREE

TISSUE DISTRIBUTION

FIGURE 4-A

CONSTRUCT NUCLEOTIDE SEQUENCE

>PFEK-D-G-HIS ERI-HCII (SEQ.ID.NO.:8)

GAATTCACCACCATGGACAGCAAAGGTTCGTCGCAGAAATCCCGCCTGCTCCTGCTGCTG
GTGGTGTCAAATCTACTCTTGTGCCAGGGTGTGGTCTCCGACTACAAGGACGACGACGAC
GTGGACGCGGCCGCTCTTGCTGCCCCCTTTGATGATGATGACAAGATCGTTGGGGGCTAT
GCTCTAGATGTGGATTCTTGGCCTTGGCAGGTCAGCATCCAGTACGACAAACAGCACGTC
TGTGGAGGGAGCATCCTGGACCCCCACTGGGTCCTCACGGCAGCCCACTGCTTCAGGAAA
CATACCGATGTGTTCAACTGGAAGGTGCGGGCAGGCTCAGACAAACTGGGCAGCTTCCCA
TCCCTGGCTGTGGCCAAGATCATCATCATTGAATTCAACCCCATGTACCCCAAAGACAAT
GACATCGCCCTCATGAAGCTGCAGTTCCCACTCACTTTCTCAGGCACAGTCAGGCCCATC
TGTCTGCCCTTCTTTGATGAGGAGCTCACTCCAGCCACCCCACTCTGGATCATTGGATGG
GGCTTTACGAAGCAGAATGGAGGGAAGATGTCTGACATACTGCTGCAGGCGTCAGTCCAG
GTCATTGACAGCACACGGTGCAATGCAGACGATGCGTACCTGGGGGAAGTCACCGAGAAG
ATGATGTGTGCAGGCATCCCGGAAGGGGGTGTGGACACCTGCCAGGGTGACAGTGGTGGG
CCCCTGATGTACCAATCTGACCAGTGGCATGTGGTGGGCATCGTTAGCTGGGGCTATGGC
TGCGGGGGCCCGAGCACCCCAGGGGTATACACCAAGGTCTCAGCCTATCTCAACTGGATC
TACAATGTCTGGAAGGCTGAGCTGTCTAGACATCACCATCACCATCACTAGCGGCCGCTT
CCCTTTAGTGAGGGTTAATGCTTCGAGCAGACATGATAAGATACATTGATGAGTTTGGAC
AAACCACAACTAGAATGCAGTGAAAAAAATGCTTTATTTGTGAAATTTGTGATGCTATTG
CTTTATTTGTAACCATTATAAGCTGCAATAAACAAGTTAGCTTGTCGAGAAGTACTAGAG
GATCATAATCAGCCATACCACATTTGTAGAGGTTTTACTTGCTTTAAAAAACCTCCCACA
CCTCCCCCTGAACCTGAAACATAAAATGAATGCAATTGTTGTTGTTAAC

FUSION PROTEIN

>PFEK-D-G-HIS (SEQ.ID.NO.:9)
MDSKGSSQKSRLLLLLVVSNLLLCQGVVSDYKDDDDVDAAALAAPFDDDDKIVGGYALDVDS
WPWQVSIQYDKQHVCGGSILDPHWVLTAAHCFRKHTDVFNWKVRAGSDKLGSFPSLAVAKII
IIEFNPMYPKDNDIALMKLQFPLTFSGTVRPICLPFFDEELTPATPLWIIGWGFTKQNGGKM
SDILLQASVQVIDSTRCNADDAYQGEVTEKMMCAGIPEGGVDTCQGDSGGPLMYQSDQWHVV
GIVSWGYGCGGPSTPGVYTKVSAYLNWIYNVWKAELSRHHHHHH

FIGURE 4-B

```
GAATTCACCACCATGGACAGCAAAGGTTCGTCGCAGAAATCCCGCCTGCTCCTGCTGCTGGTGGTGTCAAATCTACTCTTGTGCCAGGGTGTGGTCTCCG
|----+----|----+----|----+----|----+----|----+----|----+----|----+----|----+----|----+----|----+----| 100
CTTAAGTGGTGGTACCTGTCGTTTCCAAGCAGCGTCTTTAGGGCGGACGAGGACGACGACCACCACAGTTTAGATGAGAACACGGTCCCACACCAGAGGC
         M  D  S  K  G  S  S  Q  K  S  R  L  L  L  L  L  V  V  S  N  L  L  L  C  Q  G  V  V  S
         |————————————————————— Prolactin Signal Sequence ——————————————————|

Not I                                                    Xba I
ACTACAAGGACGACGACGACGTGGACGCGGCCGCTCTTGCTGCCCCCTTTGATGATGATGACAAGATCGTTGGGGGCTATGCTCTAGATGTGGATTCTTG
|----+----|----+----|----+----|----+----|----+----|----+----|----+----|----+----|----+----|----+----| 200
TGATGTTCCTGCTGCTGCTGCACCTGCGCCGGCGAGAACGACGGGGGAAACTACTACTACTGTTCTAGCAACCCCCGATACGAGATCTACACCTAAGAAC
  D  Y  K  D  D  D  D  V  D  A  A  A  L  A  A  P  F  D  D  D  D  K  I  V  G  G  Y  A  L  D  V  D  S  W
  |——— FLAG ——————————|         |—————————— EK ——————————|

GCCTTGGCAGGTCAGCATCCAGTACGACAAACAGCACGTCTGTGGAGGGAGCATCCTGGACCCCCACTGGGTCCTCACGGCAGCCCACTGCTTCAGGAAA
|----+----|----+----|----+----|----+----|----+----|----+----|----+----|----+----|----+----|----+----| 300
CGGAACCGTCCAGTCGTAGGTCATGCTGTTTGTCGTGCAGACACCTCCCTCGTAGGACCTGGGGGTGACCCAGGAGTGCCGTCGGGTGACGAAGTCCTTT
  P  W  Q  V  S  I  Q  Y  D  K  Q  H  V  C  G  G  S  I  L  D  P  H  W  V  L  T  A  A  H  C  F  R  K
                              |————————————— Protease D-G Catalytic Domain ———————————————

CATACCGATGTGTTCAACTGGAAGGTGCGGGCAGGCTCAGACAAACTGGGCAGCTTCCCATCCCTGGCTGTGGCCAAGATCATCATCATTGAATTCAACC
|----+----|----+----|----+----|----+----|----+----|----+----|----+----|----+----|----+----|----+----| 400
GTATGGCTACACAAGTTGACCTTCCACGCCCGTCCGAGTCTGTTTGACCCGTCGAAGGGTAGGGACCGACACCGGTTCTAGTAGTAGTAACTTAAGTTGG
  H  T  D  V  F  N  W  K  V  R  A  G  S  D  K  L  G  S  F  P  S  L  A  V  A  K  I  I  I  I  E  F  N
  ————————————————————————————————— Protease D-G Catalytic Domain —————————————————————

CCATGTACCCCAAAGACAATGACATCGCCCTCATGAAGCTGCAGTTCCCACTCACTTTCTCAGGCACAGTCAGGCCCATCTGTCTGCCCTTCTTTGATGA
|----+----|----+----|----+----|----+----|----+----|----+----|----+----|----+----|----+----|----+----| 500
GGTACATGGGGTTTCTGTTACTGTAGCGGGAGTACTTCGACGTCAAGGGTGAGTGAAAGAGTCCGTGTCAGTCCGGGTAGACAGACGGGAAGAAACTACT
  P  M  Y  P  K  D  N  D  I  A  L  M  K  L  Q  F  P  L  T  F  S  G  T  V  R  P  I  C  L  P  F  F  D  E
                              |————————————— Protease D-G Catalytic Domain ———————————————

GGAGCTCACTCCAGCCACCCCACTCTGGATCATTGGATGGGGCTTTACGAAGCAGAATGGAGGGAAGATGTCTGACATACTGCTGCAGGCGTCAGTCCAG
|----+----|----+----|----+----|----+----|----+----|----+----|----+----|----+----|----+----|----+----| 600
CCTCGAGTGAGGTCGGTGGGGTGAGACCTAGTAACCTACCCCGAAATGCTTCGTCTTACCTCCCTTCTACAGACTGTATGACGACGTCCGCAGTCAGGTC
  E  L  T  P  A  T  P  L  W  I  I  G  W  G  F  T  K  Q  N  G  G  K  M  S  D  I  L  L  Q  A  S  V  Q
                              |————————————— Protease D-G Catalytic Domain ———————————————

GTCATTGACAGCACACGGTGCAATGCAGACGATGCGTACCAGGGGGAAGTCACCGAGAAGATGATGTGTGCAGGCATCCCGGAAGGGGGTGTGGACACCT
|----+----|----+----|----+----|----+----|----+----|----+----|----+----|----+----|----+----|----+----| 700
CAGTAACTGTCGTGTGCCACGTTACGTCTGCTACGCATGGTCCCCCTTCAGTGGCTCTTCTACTACACACGTCCGTAGGGCCTTCCCCCACACCTGTGGA
  V  I  D  S  T  R  C  N  A  D  D  A  Y  Q  G  E  V  T  E  K  M  M  C  A  G  I  P  E  G  G  V  D  T
                              |————————————— Protease D-G Catalytic Domain ———————————————

GCCAGGGTGACAGTGGTGGGCCCCTGATGTACCAATCTGACCAGTGGCATGTGGTGGGCATCGTTAGCTGGGGCTATGGCTGCGGGGGCCCCGAGCACCCC
|----+----|----+----|----+----|----+----|----+----|----+----|----+----|----+----|----+----|----+----| 800
CGGTCCCACTGTCACCACCCGGGGACTACATGGTTAGACTGGTCACCGTACACCACCCGTAGCAATCGACCCCGATACCGACGCCCCGGGCTCGTGGGG
  C  Q  G  D  S  G  G  P  L  M  Y  Q  S  D  Q  W  H  V  V  G  I  V  S  W  G  Y  G  C  G  G  P  S  T  P
                              |————————————— Protease D-G Catalytic Domain ———————————————

Xba I                         Not I
AGGAGTATACACCAAGGTCTCAGCCTATCTCAACTGGATCTACAATGTCTGGAAGGCTGAGCTGTCTAGACATCACCATCACCATCACTAGCGGCCGCTT
|----+----|----+----|----+----|----+----|----+----|----+----|----+----|----+----|----+----|----+----| 900
TCCTCATATGTGGTTCCAGAGTCGGATAGAGTTGACCTAGATGTTACAGACCTTCCGACTCGACAGATCTGTAGTGGTAGTGGTAGTGATCGCCGGCGAA
  G  V  Y  T  K  V  S  A  Y  L  N  W  I  Y  N  V  W  K  A  E  L  S  R  H  H  H  H  H  H
  |—————————————— Protease D-G Catalytic Domain ————————————————|      |——— 6XHIS-TAG ———|

CCCTTTAGTGAGGGTTAATGCTTCGAGCAGACATGATAAGATACATTGATGAGTTTGGACAAACCACAACTAGAATGCAGTGAAAAAAATGCTTTATTTG
|----+----|----+----|----+----|----+----|----+----|----+----|----+----|----+----|----+----|----+----| 1000
GGGAAATCACTCCCAATTACGAAGCTCGTCTGTACTATTCTATGTAACTACTCAAACCTGTTTGGTGTTGATCTTACGTCACTTTTTTTTACGAAATAAAC

TGAAATTTGTGATGCTATTGCTTTATTTGTAACCATTATAAGCTGCAATAAACAAGTTAGCTTGTCGAGAAGTACTAGAGGATCATAATCAGCCATACCA
|----+----|----+----|----+----|----+----|----+----|----+----|----+----|----+----|----+----|----+----| 1100
ACTTTAAACACTACGATAACGAAATAAACATTGGTAATATTCGACGTTATTTGTTCAATCGAACAGCTCTTCATGATCTCCTAGTATTAGTCGGTATGGT

CATTTGTAGAGGTTTTACTTGCTTTAAAAAACCTCCCACACCTCCCCCTGAACCTGAAACATAAAATGAATGCAATTGTTGTTGTTAAC
|----+----|----+----|----+----|----+----|----+----|----+----|----+----|----+--->  1189
GTAAACATCTCCAAAATGAACGAAATTTTTTGGAGGGTGTGGAGGGGGACTTGGACTTTGTATTTTACTTACGTTAACAACAACAATTG
```

PAGE - WESTERN BLOT

H   = free amine
D   = D-isomer
CBO = carbobenzoxy
HHT = hexahydrotyrosyl
Z   = benzyloxycarbonyl
pNA = p-nitroanilide
DL  = D- and L- isomers

HUMAN SERINE PROTEASE D-G POLYPEPTIDE

This application claims the benefit of priority to parent application U.S. Ser. No. 09/607,745, filed Jun. 30, 2000, which issued as U.S. Pat. No. 6,750,034 on Jun. 15, 2004.

BACKGROUND OF THE INVENTION

Members of the trypsin/chymotrypsin-like (S1) serine protease family play pivotal roles in a multitude of diverse physiological processes, including digestive processes and regulatory amplification cascades through the proteolytic activation of inactive zymogen precursors. In many instances protease substrates within these cascades are themselves the inactive form, or zymogen, of a "downstream" serine protease. Well-known examples of serine protease-mediated regulation include blood coagulation, (Davie, et al. (1991). *Biochemistry* 30:10363–70), kinin formation (Proud and Kaplan (1988). *Ann Rev Immunol* 6: 49–83) and the complement system (Reid and Porter (1981). *Ann Rev Biochemistry* 50:433–464). Although these proteolytic pathways have been known for sometime, it is likely that the discovery of novel serine protease genes and their products will enhance our understanding of regulation within these existing cascades, and lead to the elucidation of entirely novel protease networks.

Proteases are used in non-natural environments for various commercial purposes including laundry detergents, food processing, fabric processing and skin care products. In laundry detergents, the protease is employed to break down organic, poorly soluble compounds to more soluble forms that can be more easily dissolved in detergent and water. In this capacity the protease acts as a "stain remover." Examples of food processing include tenderizing meats and producing cheese. Proteases are used in fabric processing, for example, to treat wool in order prevent fabric shrinkage. Proteases may be included in skin care products to remove scales on the skin surface that build up due to an imbalance in the rate of desquamation. Common proteases used in some of these applications are derived from prokaryotic or eukaryotic cells that are easily grown for industrial manufacture of their enzymes, for example a common species used is *Bacillis* as described in U.S. Pat. No. 5,217,878. Alternatively, U.S. Pat. No. 5,278,062 describes serine proteases isolated from a fungus, *Tritirachium album*, for use in laundry detergent compositions. Unfortunately use of some proteases is limited by their potential to cause allergic reactions in sensitive individuals or by reduced efficiency when used in a non-natural environment. It is anticipated that protease proteins derived from non-human sources would be more likely to induce an immune response in a sensitive individual. Because of these limitations, there is a need for alternative proteases that are less immunogenic to sensitive individuals and/or provides efficient proteolytic activity in a non-natural environment. The advent of recombinant technology allows expression of any species' proteins in a host suitable for industrial manufacture.

Herein we describe a novel serine protease isolated from small intestine termed D-G. The deduced amino acid sequence encodes a polypeptide of 435 amino acids. Interestingly, the sequence contains a hydrophobic stretch of amino acids which is a putative transmembrane near the $NH_2$-terminus. Thus, this serine protease is thought to be synthesized as a type II integral membrane protein. Alignment with other well characterized serine proteases clearly indicates that it is a member of the S1 serine protease family with the catalytic triad residing within the C-terminal half of the molecule. The protease D-G deduced amino acid sequence is most similar to the cloned serine proteases TMPRSS2 (Paoloni-Giacobino et al. (1997). *Genomics* 44:309–320) and hepsin (Leytus et al. (1988). *Biochemistry* 27:1067–74), which are also type II integral membrane proteases. We have found that the protease D-G mRNA is widely expressed in several tissues throughout the body including epidermis, fibroblasts, keratinocytes, colon, small intestine, stomach, lung, kidney, bone marrow, lymph node, thymus, ovary, prostate, uterus and spinal cord. Altered expression or regulation of this enzyme may be responsible for any one of a number of pathological conditions in these tissues. Furthermore, an up-regulation whereby under normal physiological conditions protease D-G mRNA is not expressed, and therefore undetected, but in the pathogenic condition it is markedly elevated could potentially result in initiating or exacerbation of certain diseased states. We expressed a soluble form of this novel human protease by inserting the portion of the protease D-G cDNA, encoding the catalytic domain, in a zymogen activation construct designed to permit the generic activation of heterologous serine protease catalytic domains. The result is an active preparation of protease D-G that has an activity against a subset of amidolytic substrates. Isolation of purified, enzymatically active protease D-G allows the protein to be used directly, for example to discover chemical modulators of the enzyme or as an additive in commercial products. Because protease D-G is derived from a human host, it is less likely to induce an allergic reaction in sensitive individuals, and therefore protease D-G may also be useful for formulation of compositions for laundry detergents and skin care products.

SUMMARY OF THE INVENTION

A DNA molecule encoding protease D-G has been cloned and characterized and it represents a novel serine protease. Using a recombinant expression system functional DNA molecules encoding the protease have been isolated. The biological and structural properties of these proteins are disclosed, as is the amino acid and nucleotide sequence. The recombinant DNA molecules, and portions thereof, are useful for isolating homologues of the DNA molecules, identifying and isolating genomic equivalents of the DNA molecules, and identifying, detecting or isolating mutant forms of the DNA molecules. The recombinant protein is useful to identify modulators of functional protease D-G. Modulators identified in the assays disclosed herein may be useful as therapeutic agents for cancer, skin disorders, neuropathic pain, inflammatory, or coagulation diathesis/thrombosis.

BRIEF DESCRIPTION OF THE DRAWING

FIG. 1A—The nucleotide (SEQ.ID.NO.:1) of the novel protease D-G cDNA is shown.

FIG. 1B—The amino acid sequence (SEQ.ID.NO.:2) of the novel protease D-G cDNA is shown.

The putative nucleotide polyadenylation sequence as well as the first four amino acids following the predicted zymogen activation cleavage site are underlined. The amino acid sequences of the predicted hydrophobic transmembrane domain are boxed.

Figure 2:
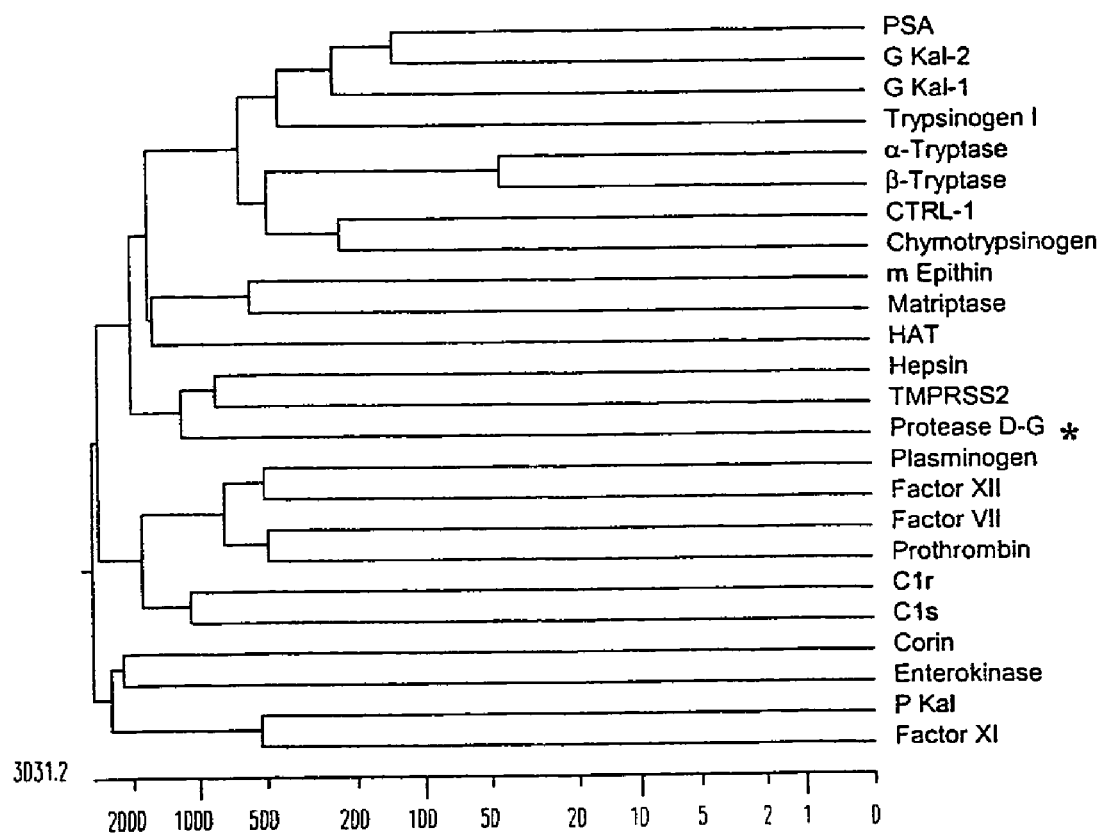

FIG. 2—The phylogenetic tree of the protease D-G amino acid sequence relative to other S1 serine proteases is shown.

Figure 3:
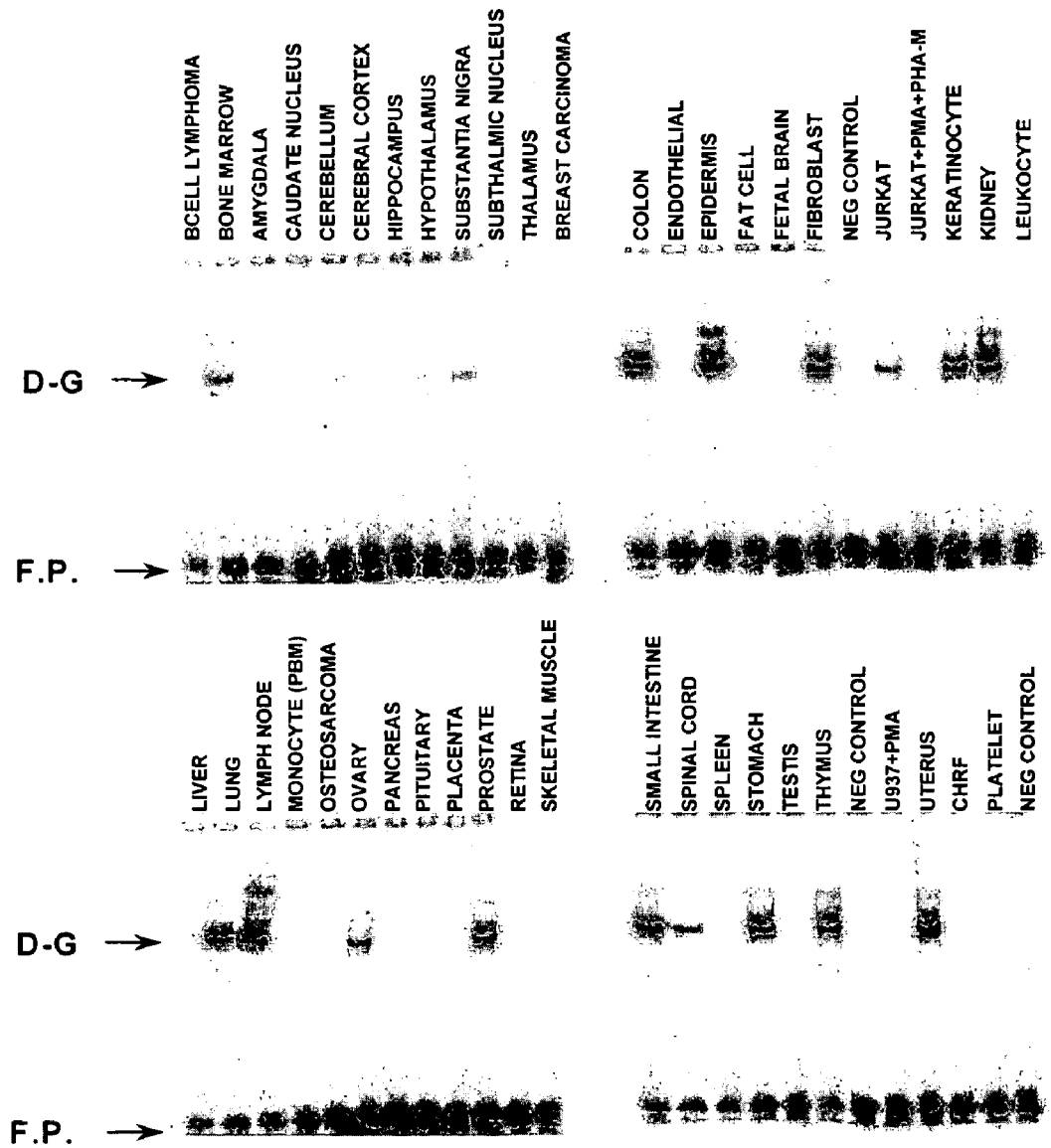

FIG. 3—PCR-based tissue distribution indicates that the protease D-G mRNA is restricted. Autoradiograms of gels are shown with the position of the D-G specific PCR product, as detected by the hybridization of a labeled nested probe, which was resolved following electrophoresis from the free probe (F.P.). The cDNA libraries of tissues and cell lines analyzed are as indicated.

FIGS. 4A & B—The nucleotide (SEQ.ID.NO.:8) and amino acid (SEQ.ID.NO.:9) sequences of the protease D-G catalytic domain in the zymogen activation construct are shown.

Figure 5:
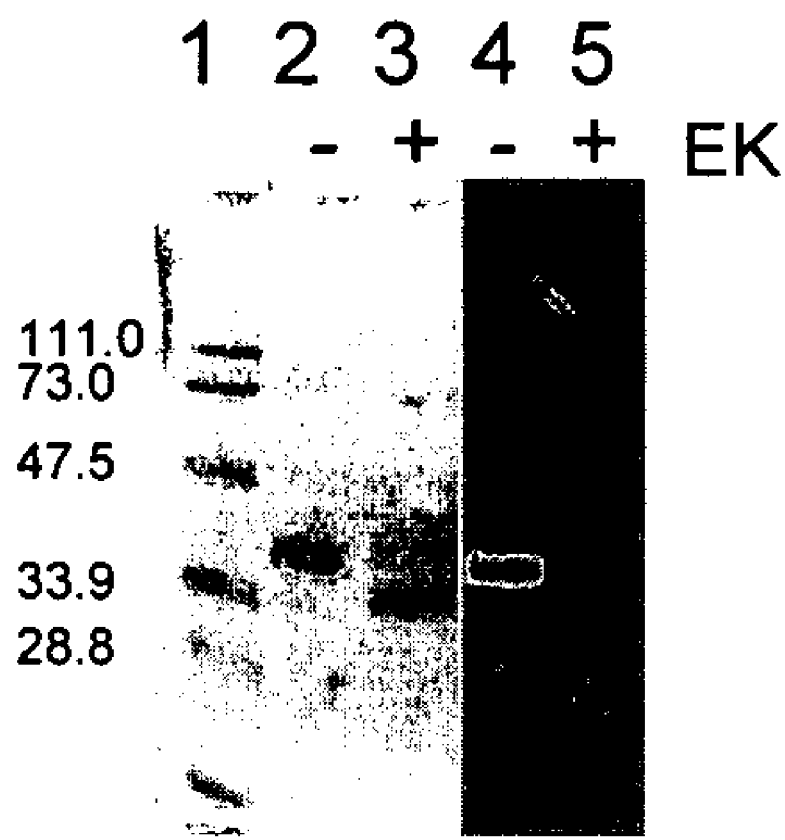

FIG. 5—Polyacrylamide gel and Western blot analyses of the purified recombinant protease PFEK-protease D-G-6× HIS. Shown is the polyacrylamide gel containing samples of the novel serine protease PFEK-protease D-G-6×HIS stained with Coomassie Brilliant Blue (lanes 2 and 3). The relative molecular masses are indicated by the positions of protein standards (lane 1). In the indicated lanes, the purified zymogen was either untreated (−) or digested (+) with enterokinase (EK) which was used to cleave and activate the zymogen of lane 1 into its active form of increased mobility shown in lane 2. Lanes 4 and 5 indicate the Western blot of the corresponding gel lanes 1 and 2, probed with the anti-FLAG MoAb M2. This demonstrates the quantitative cleavage of the expressed and purified zymogen to generate the processed and activated protease. Since the FLAG epitope is located just upstream of the of the EK pro sequence, cleavage with EK generates a FLAG-containing polypeptide which is too small to be retained in the polyacrylamide gel, and is therefore not detected in the +EK lane.

Figure 6:
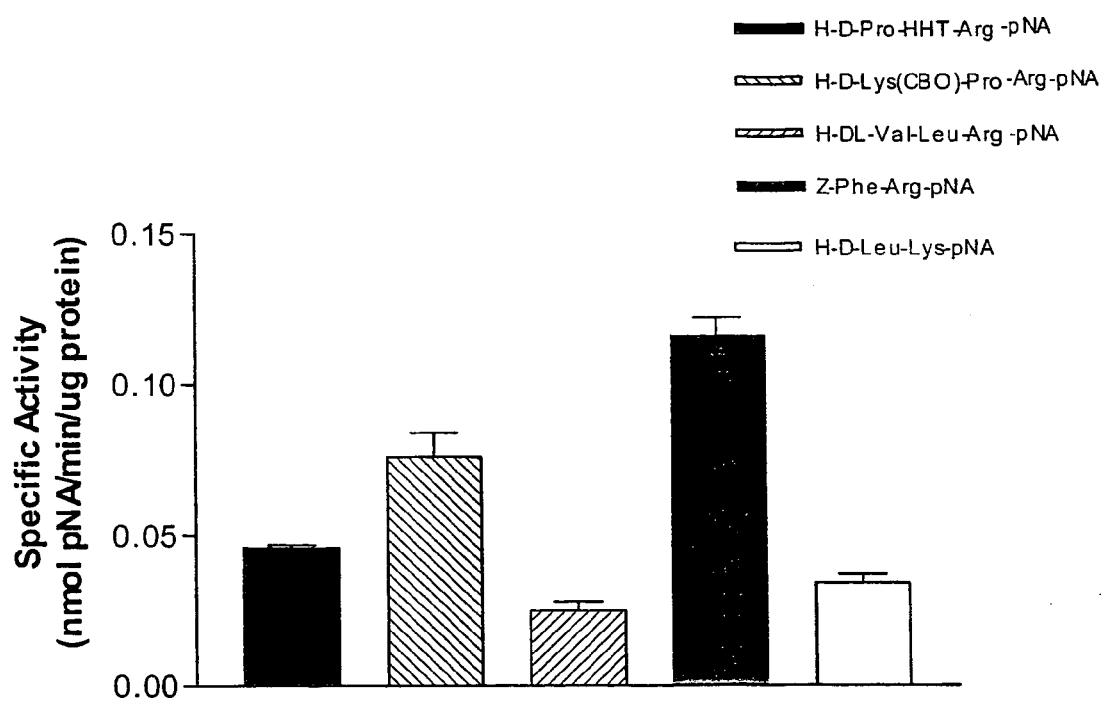

FIG. 6—Functional amidolytic activities of the recombinant protease D-G-6×HIS expressed, purified and activated from the activation construct were determined using the indicated chromogenic substrates.

DETAILED DESCRIPTION

Definitions

The term "protein domain" as used herein refers to a region of a protein that may have a particular three-dimensional structure which may be independent from the remainder of the protein. This structure may maintain a particular activity associated with the domain's function within the protein including enzymatic activity, creation of a recognition motif for another molecule, or provide necessary structural components for a protein to exist in a particular environment. Protein domains are usually evolutionarily conserved regions of proteins, both within a protein family and within protein superfamilies that perform similar functions. The term "protein superfamily" as used herein refers to proteins whose evolutionary relationship may not be entirely established or may be distant by accepted phylogenetic standards, but show similar three dimensional structure or display unique consensus of critical amino acids. The term "protein family" as used herein refers to proteins whose evolutionary relationship has been established by accepted phylogenic standards.

The term "fusion protein" as used herein refers to protein constructs that are the result of combining multiple protein domains or linker regions for the purpose of gaining the combined functions of the domains or linker regions. This is may be accomplished by molecular cloning of the nucleotide sequences encoding such domains to produce a new polynucleotide sequence that encodes the desired fusion protein. Alternatively, creation of a fusion protein may be accomplished by chemically joining two proteins.

The term "linker region" or "linker domain" or similar such descriptive terms as used herein refers to polynucleotide or polypeptide sequence that are used in the construction of a cloning vector or fusion protein. Functions of a linker region can include introduction of cloning sites into the nucleotide sequence, introduction of a flexible component or space-creating region between two protein domains, or creation of an affinity tag for specific molecule interaction. A linker region may be introduced into a fusion protein resulting from choices made during polypeptide or nucleotide sequence construction.

The term "cloning site" or "polycloning site" as used herein refers to a region of the nucleotide sequence that has one or more available restriction endonuclease consensus cleavage sequences. These nucleotide sequences may be used for a variety of purposes, including but not limited to introduction into DNA vectors to create novel fusion proteins, or to introduce specific site-directed mutations. It is well known by those of ordinary skill in the art that cloning sites can be engineered at a desired location by silent mutations, conserved mutation, or introduction of a linker region that contains desired restriction enzyme consensus sequences. It is also well known by those of ordinary skill in the art that the precise location of a cloning site can be engineered into any location in a nucleotide sequence.

The term "tag" as used herein refers to an amino acid sequence or a nucleotide sequence that encodes an amino acid sequence, that facilitates isolation, purification or detection of a protein containing the tag. A wide variety of such tags are known to those skilled in the art, and are suitable for use in the present invention. Suitable tags include, but are not limited to, HA peptide, polyhistidine peptides, biotin/avidin, and other antibody epitope binding sites.

Isolation of Protease D-G Nucleic Acid

The present invention relates to DNA encoding the human serine protease D-G which was isolated from cells of small intestine. Protease D-G, as used herein, refers to protein which can specifically function as a protease.

The complete amino acid sequence of protease D-G was not previously known, nor was the complete nucleotide sequence encoding protease D-G known. It is predicted that a wide variety of cells and cell types will contain the described protease D-G mRNA. Tissues capable of producing protease D-G include, but are not limited to epidermis, fibroblasts, keratinocytes, colon, small intestine, stomach, lung, kidney, bone marrow, lymph node, thymus, ovary, prostate, uterus and spinal cord as we have determined by a sensitive polymerase chain reaction (PCR)-mediated mRNA detection methodology.

Other cells and cell lines may also be suitable for use to isolate protease D-G cDNA. Selection of suitable cells may be done by screening for protease D-G activity in cell extracts or in whole cell assays, described herein. Cells that possess protease D-G activity in any one of these assays may be suitable for the isolation of protease D-G DNA or mRNA.

Any of a variety of procedures known in the art may be used to molecularly clone protease D-G DNA. These methods include, but are not limited to, direct functional expression of the protease D-G genes following the construction of a protease D-G-containing cDNA library in an appropriate expression vector system. Another method is to screen protease D-G-containing cDNA library constructed in a bacteriophage or plasmid shuttle vector with a labelled oligonucleotide probe designed from the amino acid sequence of the protease D-G subunits. An additional method consists of screening a protease D-G-containing cDNA library constructed in a bacteriophage or plasmid shuttle vector with a partial cDNA encoding the protease D-G protein. This partial cDNA is obtained by the specific PCR amplification of protease D-G DNA fragments through the design of degenerate oligonucleotide primers from the amino acid sequence of the purified protease D-G protein.

Another method is to isolate RNA from protease D-G-producing cells and translate the RNA into protein via an in vitro or an in vivo translation system. The translation of the RNA into a peptide a protein will result in the production of at least a portion of the protease D-G protein which can be identified by, for example, immunological reactivity with an anti-protease D-G antibody or by biological activity of protease D-G protein. In this method, pools of RNA isolated from protease D-G-producing cells can be analyzed for the presence of an RNA that encodes at least a portion of the protease D-G protein. Further fractionation of the RNA pool can be done to purify the protease D-G RNA from non-protease D-G RNA. The peptide or protein produced by this method may be analyzed to provide amino acid sequences which in turn are used to provide primers for production of protease D-G cDNA, or the RNA used for translation can be analyzed to provide nucleotide sequences encoding protease D-G and produce probes for this production of protease D-G cDNA. This method is known in the art and can be found in, for example, Maniatis, T., Fritsch, E. F., Sambrook, J. in *Molecular Cloning: A Laboratory Manual*, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating protease D-G-encoding DNA. Other types of libraries include, but are not limited to, cDNA libraries derived from other cells, from organisms other than protease D-G, and genomic DNA libraries that include YAC (yeast artificial chromosome) and cosmid libraries.

It is readily apparent to those skilled in the art that suitable cDNA libraries may be prepared from cells or cell lines which have protease D-G activity. The selection of cells or cell lines for use in preparing a cDNA library to isolate protease D-G cDNA may be done by first measuring cell associated protease D-G activity using the measurement of protease D-G-associated biological activity or a ligand binding assay.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding protease D-G may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the protease D-G gene by the above methods, the amino acid sequence of protease D-G may be necessary. To accomplish this, protease D-G protein may be purified and partial amino acid sequence determined by automated sequenators. It is not necessary to determine the entire amino acid sequence, but the linear sequence of two regions of 6 to 8 amino acids from the protein is determined for the production of primers for PCR amplification of a partial protease D-G DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the protease D-G sequence but will be capable of hybridizing to protease D-G DNA even in the presence of DNA oligonucleotides with mismatches. The mismatched DNA oligonucleotides may still sufficiently hybridize to the protease D-G DNA to permit identification and isolation of protease D-G encoding DNA. DNA isolated by these methods can be used to screen DNA libraries from a variety of cell types, from invertebrate and vertebrate sources, and to isolate homologous genes.

Purified biologically active protease D-G may have several different physical forms. protease D-G may exist as a full-length nascent or unprocessed polypeptide, or as partially processed polypeptides or combinations of processed polypeptides. The full-length nascent protease D-G polypeptide may be post-translationally modified by specific proteolytic cleavage events that results in the formation of fragments of the full length nascent polypeptide. A fragment, or physical association of fragments may have the full biological activity associated with protease D-G however, the degree of protease D-G activity may vary between individual protease D-G fragments and physically associated protease D-G polypeptide fragments.

Because the genetic code is degenerate, more than one codon may be used to encode a particular amino acid, and therefore, the amino acid sequence can be encoded by any of a set of similar DNA oligonucleotides. Only one member of the set will be identical to the protease D-G sequence but will be capable of hybridizing to protease D-G DNA even in the presence of DNA oligonucleotides with mismatches under appropriate conditions. Under alternate conditions, the mismatched DNA oligonucleotides may still hybridize to the protease D-G DNA to permit identification and isolation of protease D-G encoding DNA.

DNA encoding protease D-G from a particular organism may be used to isolate and purify homologues of protease D-G from other organisms. To accomplish this, the first protease D-G DNA may be mixed with a sample containing DNA encoding homologues of protease D-G under appropriate hybridization conditions. The hybridized DNA complex may be isolated and the DNA encoding the homologous DNA may be purified therefrom.

Functional Derivatives/Variants

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of aliphatic amino acids alanine, valine, leucine and isoleucine; interchange of the hydroxyl residues serine and threonine, exchange of the acidic residues aspartic acid and glutamic acid, substitution between the amide residues asparagine and glutamine, exchange of the basic residues lysine and arginine and variants among the aromatic residues phenylalanine, tyrosine may not cause a change in functionality of the polypeptide. Such substitutions are well known and are described, for instance in *Molecular Biology of the Gene*, 4th Ed. Bengamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residues that may result in a silent mutation, a conservative mutation, or a nonconservative mutation. Chimeric genes are prepared by swapping domains of similar or different genes to replace similar domains in the protease D-G gene. Similarly, fusion genes may be prepared that add domains to the protease D-G gene, such as an affinity tag to facilitate identification and isolation of the gene. Fusion genes may be prepared to replace regions of the protease D-G gene, for example to create a soluble version of the protein by removing a transmembrane domain or adding a targeting sequence to redirect the normal transport of the protein, or adding new post-translational modification sequences to the protease D-G gene. Examples of altered properties include but are not limited to changes in the affinity of an enzyme for a substrate or a receptor for a ligand. All such changes of the polynucleotide or polypeptide sequences are anticipated as useful variants of the present invention so long as the original function of the polynucleotide or polypeptide sequence of the present invention is maintained as described herein.

Identity or similarity, as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., (1988) SIAM J. Applied Math., 48, 1073. Methods commonly employed to determine identity or similarity between sequences include, but are not limited to those disclosed in Carillo, H., and Lipman, D., (1988) SIAM J. Applied Math., 48, 1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

Polynucleotide(s) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

The term polypeptides, as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., (1990) Meth. Enzymol. 182, 626–646 and Rattan et al., "Protein Synthesis: Posttranslational Modifications and Aging", (1992) Ann. N.Y. Acad. Sci. 663, 48–62. It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, E. coli. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

Variant(s) of polynucleotides or polypeptides, as the term is used herein, are polynucleotides or polypeptides that differ from a reference polynucleotide or polypeptide, respectively. A variant of the polynucleotide may be a naturally occurring variant such as a naturally occurring allelic variant, or it may be a variant that is not known to occur naturally. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of protease D-G is a compound that possesses a biological activity (either functional or structural) that is substantially similar to the biological activity of protease D-G. The term "functional derivatives" is intended to include the "fragments," "variants," "degenerate variants," "analogs" and "homologues" or to "chemical derivatives" of protease D-G. Useful chemical derivatives of polypeptide are well known in the art and include, for example covalent modification of reactive organic site contained within the polypeptide with a secondary chemical moiety. Well known cross-linking reagents are useful to react to amino, carboxyl, or aldehyde residues to introduce, for example an affinity tag such as biotin, a fluorescent dye, or to conjugate the polypeptide to a solid phase surface (for example to create an affinity resin). The term "fragment" is meant to refer to any polypeptide subset of protease D-G. A molecule is "substantially similar" to protease D-G if both molecules have substantially similar structures' or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire protease D-G molecule or to a fragment thereof. Particularly preferred in this regard are polynucleotides encoding variants, analogs, derivatives and fragments of SEQ ID NO.:1, and variants, analogs and derivatives of the fragments, which have the amino acid sequence of the polypeptide of SEQ ID NO.:2 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of SEQ ID NO.:1. Also especially preferred in this regard are conservative substitutions. Most highly preferred are polynucleotides encoding polypeptides having the amino acid sequence of SEQ ID NO.:2, without substitutions.

Further preferred embodiments of the invention are polynucleotides that are at least 70% identical over their entire length to a polynucleotide encoding the polypeptide having the amino acid sequence set out in SEQ ID NO.:2, and polynucleotides which are complementary to such polynucleotides. Alternatively, highly preferred are polynucleotides that comprise a region that is at least 80% identical, more highly preferred are polynucleotides at comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides which hybridize to the polynucleotides described herein in a preferred embodiment encode polypeptides which retain substantially the same biological function or activity as the polypeptide characterized by the deduced amino acid sequence of SEQ ID NO.:2. Preferred embodiments in this respect, moreover, are polynucleotides that encode polypeptides that retain substantially the same biological function or activity as the mature polypeptide encoded by the DNA of SEQ ID NO.:1. The present invention further relates to polynucleotides that hybridize to the herein above-described sequences. In this regard, the present invention especially relates to polynucleotides that hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ ID NO.:1 and to isolate cDNA and genomic clones of other genes that have a high sequence similarity to SEQ ID NO.:1. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of SEQ ID NO.:2 (in particular the mature polypeptide) as well as polypeptides which have at least 70% identity to the polypeptide of SEQ ID NO.:2, preferably at least 80% identity to the polypeptide of SEQ ID NO.:2, and more preferably at least 90% similarity (more preferably at least 90% identity) to the polypeptide of SEQ ID NO.:2 and still more preferably at least 95% similarity (still more preferably at least 97% identity) to the polypeptide of SEQ ID NO.:2 and also include portions of such polypeptides with such portion of the polypeptide generally containing at least 30 amino acids and more preferably at least 50 amino acids. Representative examples of polypeptide fragments of the invention, include, for example, truncation polypeptides of SEQ ID NO.:2. Truncation polypeptides include polypeptides having the amino acid sequence of SEQ ID NO.:2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Also preferred in this aspect of the invention are fragments characterized by structural or functional attributes of the polypeptide characterized by the sequences of SEQ ID NO.:2. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity.

Recombinant Expression of Protease D-G

The cloned protease D-G DNA obtained through the methods described herein may be recombinantly expressed by molecular cloning into an expression vector containing a suitable promoter and other appropriate transcription regulatory elements, and transferred into prokaryotic or eukaryotic host cells to produce recombinant protease D-G protein. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant protease D-G in mammalian cells. Commercially available mammalian expression vectors which may be suitable for recombinant protease D-G expression, include but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant protease D-G in bacterial cells. Commercially available bacterial expression vectors which may be suitable for recombinant protease D-G expression include, but are not limited to pET vectors (Novagen) and pQE vectors (Qiagen).

A variety of fungal cell expression vectors may be used to express recombinant protease D-G in fungal cells such as yeast. Commercially available fungal cell expression vectors which may be suitable for recombinant protease D-G expression include but are not limited to pYES2 (Invitrogen) and Pichia expression vector (Invitrogen).

A variety of insect cell expression vectors may be used to express recombinant protease D-G in insect cells. Commercially available insect cell expression vectors which may be suitable for recombinant expression of protease D-G include but are not limited to pBlueBacII (Invitrogen).

DNA encoding protease D-G may be cloned into an expression vector for expression in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to drosophila and silkworm derived cell lines.

Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce protease D-G protein. Identification of protease D-G expressing host cell clones may be done by several means, including but not limited to immunological reactivity with anti-protease D-G antibodies, and the presence of host cell-associated protease D-G activity.

Expression of protease D-G DNA may also be performed using in vitro produced synthetic mRNA. Synthetic mRNA or mRNA isolated from protease D-G producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the protease D-G DNA sequence(s) that yields optimal levels of protease D-G activity and/or protease D-G protein, protease D-G DNA molecules including, but not limited to, the following can be constructed: the full-length open reading frame of the protease D-G cDNA encoding the [~48 kDa] protein from approximately base [277] to approximately base [1581] (these numbers correspond to first nucleotide of first methionine and last nucleotide before the first stop codon) and several constructs containing portions of the cDNA encoding protease D-G protein. All constructs can be designed to contain none, all or portions of the 5' or the 3' untranslated region of protease D-G cDNA. Protease D-G activity and levels of protein expression can be determined following the introduction, both singly and in combination, of these constructs into appropriate host cells. Following determination of the protease D-G DNA cassette yielding optimal expression in transient assays, this protease D-G DNA construct is transferred to a variety of expression vectors, for expression in host cells including, but not limited to, mammalian cells, baculovirus-infected insect cells, E. coli, and the yeast S. cerevisiae.

Assay Methods for Protease D-G

Host cell transfectants and microinjected oocytes may be used to assay both the levels of functional protease D-G activity and levels of total protease D-G protein by the following methods. In the case of recombinant host cells, this involves the co-transfection of one or possibly two or more plasmids, containing the protease D-G DNA encoding one or more fragments encoding the catalytic domain. In the case of oocytes, this involves the co-injection of synthetic RNAs for protease D-G protein. Following an appropriate period of time to allow for expression, cellular protein is metabolically labelled with, for example $^{35}$S-methionine for 24 hours, after which cell lysates and cell culture supernatants are harvested and subjected to immunoprecipitation with polyclonal antibodies directed against the protease D-G protein.

Levels of protease D-G protein in host cells are quantitated by immunoaffinity and/or proteolytic/amidolytic assay techniques. Cells expressing protease D-G can be assayed for the number of protease D-G molecules expressed by measuring the amount of proteolytic/amidolytic activity. Protease D-G-specific affinity beads or protease D-G-specific antibodies are used to isolate for example $^{35}$S-methionine labelled or unlabelled protease D-G protein. Labelled protease D-G protein is analyzed by SDS-PAGE. Unlabelled protease D-G protein is detected by Western blotting, ELISA or RIA assays employing protease D-G specific antibodies.

Cell Based Assays

The present invention provides a whole cell method to detect compound modulation of protease D-G. The method comprises the steps;

1) contacting a compound, and a cell that contains functional protease D-G or purifying functional protease D-G, and 2) measuring a change in the cell in response or protease D-G activity by the compound.

The amount of time necessary for protease D-G interaction with the compound is empirically determined, for example, by running a time course with a known protease D-G modulator and measuring cellular/activity changes as a function of time.

The term "cell" refers to at least one cell, but includes a plurality of cells appropriate for the sensitivity of the detection method. Cells suitable for the present invention may be bacterial, yeast, or eukaryotic.

The assay methods to determine compound modulation of functional protease D-G can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The cellular changes suitable for the method of the present invention comprise directly measuring changes in the function or quantity of protease D-G, or by measuring downstream effects of protease D-G function, for example by measuring secondary messenger concentrations or changes in transcription or by changes in protein levels of genes that are transcriptionally influenced by protease D-G, or by measuring phenotypic changes in the cell. Preferred measurement means include changes in the quantity of protease D-G protein, changes in the functional activity of protease D-G, changes in the quantity of mRNA, changes in intracellular protein, changes in cell surface protein, or secreted protein, or changes in Ca+2, cAMP or GTP concentration. Changes in the quantity or functional activity of protease D-G are described herein. Changes in the levels of mRNA are detected by reverse transcription polymerase chain reaction (RT-PCR) or by differential gene expression. Immunoaffinity, ligand affinity, or enzymatic measurement quantifies changes in levels of protein in host cells. Protein-specific affinity beads or specific antibodies are used to isolate for example $^{35}$S-methionine labelled or unlabelled protein. Labelled protein is analyzed by SDS-PAGE. Unlabelled protein is detected by Western blotting, cell surface detection by fluorescent cell sorting, cell image analysis, ELISA or RIA employing specific antibodies. Where the protein is an enzyme, the induction of protein is monitored by cleavage of a flourogenic or colorimetric substrate.

Preferred detection means for cell surface protein include flow cytometry or statistical cell imaging. In both techniques the protein of interest is localized at the cell surface, labeled with a specific fluorescent probe, and detected via the degree of cellular fluorescence. In flow cytometry, the cells are analyzed in a solution, whereas in cellular imaging techniques, a field of cells is compared for relative fluorescence.

A preferred detection means for secreted proteins that are enzymes such as alkaline phosphatase or proteases, would be fluorescent or colorimetric enzymatic assays. Fluorescent/luminescent/color substrates for alkaline phosphatase are commercially available and such assays are easily adaptable to high throughput multiwell plate screen format. Fluorescent energy transfer based assays are used for protease assays. Fluorophore and quencher molecules are incorporated into the two ends of the peptide substrate of the protease. Upon cleavage of the specific substrate, separation of the fluorophore and quencher allows the fluorescence to be detectable. When the secreted protein could be measure by radioactive methods, scintillation proximity technology could be used. The substrate of the protein of interest is immobilized either by coating or incorporation on a solid support that contains a fluorescent material. A radioactive molecule, brought in close proximity to the solid phase by enzyme reaction, causes the fluorescent material to become excited and emit visible light. Emission of visible light forms the basis of detection of successful ligand/target interaction, and is measured by an appropriate monitoring device. An example of a scintillation proximity assay is disclosed in U.S. Pat. No. 4,568,649, issued Feb. 4, 1986. Materials for these types of assays are commercially available from Dupont NEN® (Boston, Mass.) under the trade name FlashPlate™.

A preferred detection means where the endogenous gene results in phenotypic cellular structural changes is statistical image analysis the cellular morphology or intracellular phenotypic changes. For example, but not by way of limitation, and cell may change morphology such a rounding versus remaining flat against a surface, or may become growth-surface independent and thus resemble transformed cell phenotype well known in the art of tumor cell biology, or a cell may produce new outgrowths. Phenotypic changes that may occur intracellularly include cytoskeletal changes, alteration in the entoplasmic reticulum/Golgi complex in response to new gene transcription, or production of new vesicles.

Where the endogenous gene encodes a soluble intracellular protein, changes in the endogenous gene may be measured by changes of the specific protein contained within the cell lysate. The soluble protein may be measured by the methods described herein.

The present invention is also directed to methods for screening for compounds that modulate the expression of DNA or RNA encoding protease D-G as well as the function of protease D-G protein in vivo. Compounds may modulate by increasing or attenuating the expression of DNA or RNA encoding protease D-G, or the function of protease D-G protein. Compounds that modulate the expression of DNA or RNA encoding protease D-G or the function of protease D-G protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, and protease D-G.

Purification of Protease D-G Protein

Following expression of protease D-G in a recombinant host cell, protease D-G protein may be recovered to provide purified protease D-G in active form. Several protease D-G purification procedures are available and suitable for use (add references for purification of similar proteins that could be the basis of a purification scheme). As described above for purification of protease D-G from natural sources, recombinant protease D-G may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography, lectin chromatography, and antibody/ligand affinity chromatography.

Recombinant protease D-G can be separated from other cellular proteins by use of an immunoaffinity column made with monoclonal or polyclonal antibodies specific for full length nascent protease D-G, polypeptide fragments of protease D-G or protease D-G subunits. The affinity resin is then equilibrated in a suitable buffer, for example phosphate buffered saline (pH 7.3), and the cell culture supernatants or cell extracts containing protease D-G or protease D-G subunits are slowly passed through the column. The column is then washed with the buffer until the optical density ($A_{280}$) falls to background, then the protein is eluted by changing the buffer condition, such as by lowering the pH using a buffer such as 0.23 M glycine-HCl (pH 2.6). The purified protease D-G protein is then dialyzed against a suitable buffer such as phosphate buffered saline.

Protein Based Assay

The present invention provides an in vitro protein assay method to detect compound modulation of protease D-G protein activity. The method comprises the steps;

1) contacting a compound, and function protease D-G protein, and 2) measuring a change to protease D-G function by the compound.

The amount of time necessary for cellular contact with the compound is empirically determined, for example, by running a time course with a known protease D-G modulator and measuring changes as a function of time.

This Section is Directed to Protease Assays

Methods for detecting compounds that modulate protease D-G proteolytic activity comprise combining a punitive modulating compound, functional protease D-G protein, and a suitable labeled substrate and monitoring an effect of the compound on the protease by changes in the amount of substrate either as a function of time or after a predefined period of time. Labeled substrates include, but are not limited to; substrate that is radiolabeled (Coolican et al. (1986). *J. Biol. Chem.* 261:4170–6), fluorometric (Lonergan et al. (1995). *J. Food Sci.* 60:72–3, 78; Twining (1984). *Anal. Biochem.* 143:30–4) or colorimetric (Buroker-Kilgore and Wang (1993). *Anal. Biochem.* 208:387–92). Radioisotopes useful for use in the present invention include those well known in the art, specifically $^{125}$I, $^{131}$I, $^{3}$H, $^{14}$C, $^{35}$S, $^{32}$P, and $^{33}$P. Radioisotopes are introduced into the peptide by conventional means, such as iodination of a tyrosine residue, phosphorylation of a serine or threonine residue, or incorporation of tritium, carbon or sulfur utilizing radioactive amino acid precursors. Zymography following SDS polyacrylamide gel electrophoresis (Wadstroem and Smyth (1973). *Sci. Tools* 20:17–21), as well as by fluorescent resonance energy transfer (FRET)-based methods (Ng and Auld (1989). *Anal. Biochem.* 183:50–6) are also methods used to detect compounds that modulate protease D-G proteolytic activity. Compounds that are agonists will increase the rate of substrate degradation and will result in less remaining substrate as a function of time. Compounds that are antagonists will decrease the rate of substrate degradation and will result in greater remaining substrate as a function of time.

A preferred assay format useful for the method of the present invention is a FRET based method using peptide substrates that contain a fluorescent donor with either a quencher or acceptor that are separated by a peptide sequence encoding the protease D-G cleavage site. A fluorescent donor is a fluorogenic compound that can adsorb energy and transfers a portion of the energy to another compound. Examples of fluorescent donors suitable for use in the present invention include, but are not limited to, coumarins, xanthene dyes such as fluoresceines, rhodols, and rhodamines, resorufins, cyanine dyes bimanes, acridines, isoindols, dansyl dyes, aminophthalic hydrazides such as luminol and isoluminol derivatices, aminophthalimides, aminonapthalimides, aminobenzofurans, aminoquinolines, dicanohydroquinones, and europium and terbium complexes and related compounds. A quencher is a compound that reduces the emission from the fluorescent donor when it is appropriately proximally located to the donor, and do not generally re-emit the energy in the form of fluorescence. Examples of such moieties include indigos, bezoquinones, anthraquinones, azo compounds, nitro compounds, indoanilines, and di- and triphenylmethanes. A FRET method using a donor/quencher pair measures increased emission from the fluorescent donor as a function of protease D-G enzymatic activity upon the peptide substrate. Therefore a test compound that antagonizes protease D-G will generate an emission signal between two control samples—a low (basal) fluorescence from the FRET peptide alone and a higher fluorescence from the FRET peptide digested by the activity of enzymatically active protease D-G. An acceptor is a fluorescent molecule that adsorbs energy from the fluorescent donor and re-emits a portion of the energy as fluorescence. An acceptor is a specific type of quencher that enables a separate mechanism to measure protease D-G proteolytic efficacy. Methods that utilize a donor/acceptor pair measure a decrease in acceptor emission as a function of protease D-G enzymatic activity upon the peptide substrate. Therefore a test compound that antagonizes protease D-G will generate an emission signal between two control samples—a higher basal fluorescence from the FRET peptide alone and a lower fluorescence from the FRET peptide digested by the activity of enzymatically active protease D-G. Examples of acceptor useful for methods of the present invention include, but are not limited to, coumarins, fluoresceins, rhodols, rhodamines, resorufins, cyanines, difuoroboradiazindacenes, and phthalcyanines.

Production and Use of Antibodies that Bind to Protease D-G

Monospecific antibodies to protease D-G are purified from mammalian antisera containing antibodies reactive against protease D-G or are prepared as monoclonal antibodies reactive with protease D-G using the technique originally described by Kohler and Milstein, *Nature* 256: 495–497 (1975). Immunological techniques are well known in the art and described in, for example, *Antibodies: A laboratory manual* published by Cold Spring Harbor Laboratory Press, Cold Spring Harbor, N.Y., ISBN 0879693142. Monospecific antibody as used herein is defined as a single antibody species or multiple antibody species with homogenous binding characteristics for protease D-G. Homogenous binding as used herein refers to the ability of the antibody species to bind to a specific antigen or epitope, such as those associated with the protease D-G, as described above. protease D-G specific antibodies are raised by immunizing animals such as mice, rats, guinea pigs, rabbits, goats, horses and the like, with rabbits being preferred, with an appropriate concentration of protease D-G either with or without an immune adjuvant.

Preimmune serum is collected prior to the first immunization. Each animal receives between about 0.001 mg and about 1000 mg of protease D-G associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of protease D-G in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with protease D-G are prepared by immunizing inbred mice, preferably Balb/c, with protease D-G. The mice are immunized by the IP or SC route with about 0.001 mg to about 1.0 mg, preferably about 0.1 mg, of protease D-G in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 to about 1.0 mg of protease D-G in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using protease D-G as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1\times10^6$ to about $6\times10^6$ hybridoma cells at least about 4 days after priming. Ascites fluid is collected at approximately 8–12 days after cell transfer and the monoclonal antibodies are purified by techniques known in the art.

In vitro production of anti-protease D-G mAb is carried out by growing the hybridoma in tissue culture, media well known in the art. High density in vitro cell culture may be conducted to produce large quantities of anti-protease D-G mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of protease D-G in body fluids or tissue and cell extracts.

It is readily apparent to those skilled in the art that the above described methods for producing monospecific antibodies may be utilized to produce antibodies specific for protease D-G polypeptide fragments, or full-length nascent protease D-G polypeptide, or the individual protease D-G subunits. Specifically, it is readily apparent to those skilled in the art that monospecific antibodies may be generated which are specific for only one protease D-G subunit or the fully functional protease D-G protein. It is also apparent to those skilled in the art that monospecific antibodies may be generated that inhibit normal function of protease D-G protein.

Protease D-G antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfhydryl groups on antibodies are well known in the art; amine groups are reactive with, for example, N-hydroxysuccinimide esters.

The aberrant expression or regulation of proteolytic activity can result in numerous pathophysiological states. For example several bleeding disorders, resulting from genetic lesions, are known to be caused by the deficiency in any one of a number of active serine protease coagulation factors. Many cancerous cells and tumors over-express proteases, several of which have been identified as serine proteases. These enzymes are thought to facilitate tumor growth and/or metastasis. Likewise, serine proteases identified in the skin are perceived to have a role in tissue remodeling and desquamation. Many cells of the immune system produce and secrete serine proteases that are likely to function during inflammatory conditions. In general, these serine proteases are thought to act by extracellular matrix degradation or by the specific activation of pro-hormone precursors. into active growth regulators or chemoattractants. Thus it is easy to imagine how modulators of serine protease activity could have profound effects of various pathophysiological conditions.

Kit Compositions Containing Protease D-G Specific Reagents

Kits containing protease D-G DNA or RNA, antibodies to protease D-G, or protease D-G protein may be prepared. Such kits are used to detect DNA which hybridizes to protease D-G DNA or to detect the presence of protease D-G protein or peptide fragments in a sample. Such characterization is useful for a variety of purposes including but not limited to forensic analyses, diagnostic applications, and epidemiological studies.

The DNA molecules, RNA molecules, recombinant protein and antibodies of the present invention may be used to screen and measure levels of protease D-G DNA, protease D-G RNA or protease D-G protein. The recombinant proteins, DNA molecules, RNA molecules and antibodies lend themselves to the formulation of kits suitable for the detection and typing of protease D-G. Such a kit would comprise a compartmentalized carrier suitable to hold in close confinement at least one container. The carrier would further comprise reagents such as recombinant protease D-G protein or anti-protease D-G antibodies suitable for detecting protease D-G. The carrier may also contain a means for detection such as labeled antigen or enzyme substrates or the like.

Gene Therapy

Nucleotide sequences that are complementary to the protease D-G encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other protease D-G antisense oligonucleotide mimetics. protease D-G antisense molecules may be introduced into cells by microinjection, liposome encapsulation or by expression from vectors harboring the antisense sequence. protease D-G antisense therapy may be particularly useful for the treatment of diseases where it is beneficial to reduce protease D-G activity.

protease D-G gene therapy may be used to introduce protease D-G into the cells of target organisms. The protease D-G gene can be ligated into viral vectors that mediate transfer of the protease D-G DNA by infection of recipient host cells. Suitable viral vectors include retrovirus, adenovirus, adeno-associated virus, herpes virus, vaccinia virus, polio virus and the like. Alternatively, protease D-G DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo protease D-G gene therapy. protease D-G gene therapy may be particularly useful for the treatment of diseases where it is beneficial to elevate protease D-G activity. Protocols for molecular methodology of gene therapy suitable for use with the protease D-G gene is described in *Gene Therapy Protocols*, edited by Paul D. Robbins, Human press, Totawa N.J., 1996.

Pharmaceutical Compositions

Pharmaceutically useful compositions comprising protease D-G DNA, protease D-G RNA, or protease D-G protein, or modulators of protease D-G receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of protease D-G-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the protease D-G receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of protease D-G can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a protease D-G modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the protease D-G receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyl-eneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Plasmid Manipulations

All molecular biological methods were in accordance with those previously described (Maniatis et al. (1989). 1–1626). Oligonucleotides were purchased from Ransom Hill Biosciences (Ransom Hill, Calif.) and all restriction endonucleases and other DNA modifying enzymes were from New England Biolabs (Beverly, Mass.) unless otherwise specified. The protease D-G expression construct was made in the baculovirus expression vector pFastBac1 (Life Technologies, Gaithersberg, Md.) as described below. All construct manipulations were confirmed by dye terminator cycle sequencing using Allied Biosystems 377 fluorescent sequencers (Perkin Elmer, Foster City, Calif.).

Acquisition of Protease D-G cDNA

A recombinant phage containing the protease D-G cDNA was isolated from a human small intestine library (Clontech, Palo Alto, Calif.). The insert was subjected to sequence analysis and it was found to contain an open reading frame of 1305 nucleotides excluding the TAA stop codon (SEQ ID NO.:1), which had homology to S1 serine proteases. Significantly, the open reading frame is likely to be authentic since it is preceded by an in-frame TGA stop codon at position 157. This clone is also likely to contain the entire 3' untranslated since a putative polyadenylation sequence (AT- TAAA) with a good match to the known sequence was (AATAAA) was also identified just upstream of a poly A stretch. The deduced open reading frame encodes a preproD-G protein of 435 amino acids (SEQ ID NO.:2), with an estimated molecular mass ($M_r$) of about 48-Kd, and a strong homology to other serine proteases. Additional sequence analysis of the protease D-G amino acid sequence predicted a transmembrane segment near the amino terminus (residues 31–52 in SEQ ID NO.:2), suggesting that this novel cDNA encoded a type II transmembrane serine protease. Homology searches of the Genbank database with the protease D-G cDNA indicated that this was a novel cDNA had closest similarity to the cloned serine proteases TMPRSS2 (Paoloni-Giacobino et al. (1997). *Genomics* 44:309–320) and hepsin (Leytus et al. (1988). *Biochemistry* 27:1067–74), which are also type II integral membrane proteases. The zymogen activation sequence is very similar to that of other S1 serine proteases and predicts a mature protein of 233 amino acids. The catalytic triad residues H, D and S of protease D-G are located at positions 243, 339 and 385, respectively (using the methionine initiator of the prepro D-G sequence as number one). A phylogenetic tree of the deduced protease D-G amino acid sequence with other members of the S1 serine protease family was generated by the Clustal W program (Higgins and Sharp (1989). *Comput. Appl. Biosci.* 5:151–3) shown in FIG. 2 as determined using the MegAlign 3.1.7 program (DNASTAR Inc., Madison, Wis.).

EXAMPLE 2

Tissue Distribution of the Protease D-G mRNA

We employed a highly sensitive PCR profiling technique to identify the tissue distribution of protease D-G mRNA. For this application, several human cDNA libraries (all were from Clontech, (Palo Alto, Calif.) except the CHRF-288 megakaryocytic cell line and human gel filtered platelet libraries which we constructed using the ZAP Express cDNA system (Stratagene, La Jolla, Calif.). The PCR primers for the profiling analysis were as follows:

```
SEQ.ID.NO.3:    5'-ACAGCCTCAGCATTTCTTGG-3'

SEQ.ID.NO.4:    5'-TCTTGCTCTAGTAGGCTTGG-3'
```

Briefly, the 50 µl PCR reactions used 1 µl of diluted phage stock (~$10^8$ to $10^{10}$ pfu/ml) from each of the cDNA libraries tested. Reactions were initially denatured at 94° C. for 5 min. and subjected to 35 cycles of 94° C. for 20 sec.; 56° C. for 20 sec.; and then 72° C. for 30 sec. followed by a final 72° C. elongation for 10 min. A nested primer probe of the sequence SEQ.ID.NO.5: 5'-TTGGTGCTCCCAGCATCCCAGGGAGAGACACAGCCCACTG-3' was radiolabeled using gamma $^{32}$P-ATP and T4 polynucleotide kinase (Life Technologies, Gaithersberg, Md.) and unincorporated label was removed, following the reaction, using a QIAquick nucleotide removal column (Qiagen, Valencia, Calif.). The $^{32}$P end-labeled nested primer probe ($1\times10^5$ cpm) was combined with 10 µl of each sample following the PCR reaction. The PCR product-probe mixtures were denatured at 94° C. for 5 min.; hybridized at 60° C. for 15 minutes, and cooled to 4° C. The annealed samples (10 µl) were electrophoresed in 6% Tris-Borate-EDTA non-denaturing polyacrylamide gels (Novex), dried and exposed by autoradiography. A PCR profile of the cDNA libraries used in FIG. 3 with beta-actin PCR primers and labeled nested primer probe produced a beta-actin PCR product in all samples examined.

As seen in FIG. 3, the distribution of protease D-G mRNA is highly restricted to specific tissues and cell types. The tissue types expressing the protease D-G transcript are epidermis, fibroblasts, keratinocytes, colon, small intestine, stomach, lung, kidney, bone marrow, lymph node, thymus, ovary, prostate, uterus and spinal cord. Of particular significance is that D-G protease mRNA is not expressed in pancreas or liver, tissues normally found to express numerous serine protease genes.

EXAMPLE 3

Construct Generation for the Expression of Active Protease D-G

Since members of the S1 protease family are most often synthesized as inactive zymogen precursors, and require limited proteolysis to become proteolytically active, we have developed a zymogen activation construct to express and permit the generic activation of heterologous serine protease cDNAs. This construct features a bovine preprolactin signal sequence fused in-frame with the MoAb M2 anti-FLAG antibody epitope as previously described (Ishii et al. (1993). *J. Biol. Chem.* 268:9780–6) for the purposes of secretion and antibody detection respectively (PF). Significantly, this construct also contains the enterokinase cleavage site from human trypsinogen I (EK) fused in-frame and downstream from the signal sequence. At the C-terminus, preceding a stop codon, is an additional sequence encoding 6 histidine (6×HIS) codons for affinity purification on nickel resins respectively. A unique Xba I restriction enzyme site, immediately upstream of the affinity tag sequence and downstream of the PFEK prepro sequence described above, and is the point of in-frame insertion of the catalytic domain of a heterologous serine protease cDNA (FIG. 4). The zymogen activation vector described above has been cloned into a modified pFastBac1 transplacement plasmid to generate PFEK-6×HIS-TAG FB.

The purified plasmid DNA of the full length protease D-G cDNA was used as a template in a 100 µl preparative PCR reaction using the Native Pfu Polymerase (Stratagene, La Jolla, Calif.) in accordance with the manufacturer's recommendations. The primers used SEQ.ID.NO.6: D-G Xba-U 5'-ATGCTCTAGATGTGGATTCTTGGCCTTGGC-3' SEQ.ID.NO.7: D-G Xba-L 5'-GATGTCTAGACAGCTCAGCCTTCCAGACATTG-3' contained Xba I cleavable ends, and were designed to flank the catalytic domain of protease D-G and generate the protease D-G Xba I catalytic cassette. The preparative PCR reaction was run at 18 cycles of 94° C. for 30 sec.; 60° C. for 30 sec; 72° C. for 2.0 min.

The preparative PCR product was phenol/CHCl$_3$ (1:1) extracted once, CHCl$_3$ extracted, and then EtOH precipitated with glycogen (Boehringer Mannheim Corp., Indianapolis, Ind.) and carrier. The precipitated pellet was rinsed with 70% EtOH, dried by vacuum, and resuspended in 80 ul H$_2$O, 10 ul 10 restriction buffer number 2 and 1 ul 100×BSA (New England Biolabs, Beverly, Mass.). The product was digested for 3 hr. at 37° C. with 200 units Xba I restriction enzyme (New England Biolabs, Beverly, Mass.). The Xba I digested product was phenol/CHCl$_3$ (1:1) extracted once, CHCl$_3$ extracted, EtOH precipitated, rinsed with 70% EtOH, and dried by vacuum. For purification from contaminating template plasmid DNA, the product was electrophoresed through 1.0% low melting temperature agarose (Life Technologies, Gaithersberg, Md.) gels in TAE buffer (40 mM Tris-Acetate, 1 mM EDTA pH 8.3) and excised from the gel. An aliquot of the excised product was then used for in-gel ligations with the Xba I digested, dephosphorylated and gel purified, zymogen activation vector described above. Clones containing the D-G Xba cassette, inserted in the correct orientation to generate the construct PFEK-protease D-G-6xHIS-TAG 64, were confirmed by sequence analyses to ensure that the proper translational register with respect to the $NH_2$-terminal PFEK prepro sequence and C-terminal 6xHIS affinity tag was maintained.

EXAMPLE 4

Expression of Recombinant Protease D-G

The recombinant bacmid containing the PFEK-protease D-G-6xHIS construct was prepared from bacterial transformation, selection, growth, purification and PCR confirmation in accordance with the manufacturer's recommendations. Cultured Sf9 insect cells (ATCC CRL-1711) were transfected with purified bacmid DNA and several days later, conditioned media containing recombinant PFEK-protease D-G-6xHIS baculovirus was collected for viral stock amplification. Sf9 cells growing in Sf-900 II SFM at a density of $2 \times 10^6$/ml were infected at a multiplicity of infection of 2 at 27° C. for 80 hours, and media was collected and concentrated for purification of PFEK-protease D-G-6xHIS.

EXAMPLE 5

Purification, and Activation of Recombinant Protease D-G

Culture supernatants from baculovirus infected Sf9 cells expressing PFEK-D-G-6xHIS were concentrated and desalted at 4° C. using a Centricon Plus-80 Biomax-8 concentrator (Millipore, Marlborough, Mass.). Ni-NTA (150 µl of a 50% slurry/per 100 µg of zymogen) (Qiagen, Valencia, Calif.) was added to 5 ml the concentrated sample and mixed by shaking at 4° C. for 60 min. The zymogen-bound resin was washed 3 times with wash buffer [10 mM Tris-HCl (pH 8.0), 300 mM NaCl, and 15 mM imidazole], followed by with a 1.5 ml wash with ds $H_2O$. Zymogen cleavage was carried out by adding enterokinase (10 U per 50 µg of zymogen) (Novagen, Inc., Madison Wis.; or Sigma, St. Louis, Mo.) to the zymogen-bound Ni-NTA beads in a small volume at room temperature overnight with gentle shaking in a buffer containing 20 mM Tris-HCl (pH 7.4), 50 mM NaCl, and 2.0 mM $CaCl_2$. The resin was then washed twice with 1.5 ml wash buffer. The activated protease D-G-6xHIS was eluted with elution buffer [20 mM Tris-HCl (pH 7.8), 250 mM NaCl, and 250 mM imidazole]. Eluted protein concentration was determined by a Micro BCA Kit (Pierce, Rockford, Ill.) using bovine serum albumin as a standard.

Electrophoresis and Western Blotting Detection of Recombinant Proteases D-G

Samples of the purified PFEK-protease D-G-6xHIS zymogen or activated protease D-G-6xHIS, denatured in the presence of the reducing agent dithiothreitol (DTT), were analyzed by SDS-PAGE (Bio Rad, Hercules Calif.) stained with Coomassie Brilliant Blue. For Western blotting, gels were electrotransferred to Hybond ECL membranes (Amersham, Arlington Heights, Ill.). The FLAG-tagged PFEK-protease D-G-6xHIS zymogen expressed from infected Sf9 cells was detected with anti-Flag M2 antibody (Babco, Richmond, Calif.). The secondary antibody was a goat-anti-mouse IgG (H+L), horseradish peroxidase-linked $F(ab')_2$ fragment, (Boehringer Mannheim Corp., Indianapolis, Ind.) and was detected by the ECL kit (Amersham, Arlington Heights, Ill.).

EXAMPLE 6

Chromogenic Assay of Activated Recombinant Proteases D-G

Amidolytic activities of the activated serine proteases are monitored by release of para-nitroaniline (pNA) from synthetic substrates that are commercially available (Bachem California Inc., Torrance, Pa.; American Diagnostica Inc., Greenwich, Conn.; Kabi Pharmacia Hepar Inc., Franklin, Ohio). Assay mixtures contain chromogenic substrates in 500 uM and 10 mM TRIS-HCl (pH 7.8), 25 mM NaCl, and 25 mM imidazole. Release of pNA is measured over 120 min at 37° C. on a micro-plate reader (Molecular Devices, Menlo Park, Calif.) with a 405 nm absorbance filter. The initial reaction rates (Vmax, mOD/min) are determined from plots of absorbance versus time using Softmax (Molecular Devices, Menlo Park, Calif.). The specific activities (nmole pNA produced/min/ug protein) of the activated protease D-G-6xHIS for the various substrates are presented in Table 1. No measurable chromogenic amidolytic activity was detected with the purified unactivated PFEK-protease D-G-6xHIS zymogen.

TABLE 1

SPECIFIC ACTIVITY TABLE
The specific activity (nmole pNA produced/min/ug protein) of recombinant activated protease D-G-6XHIS, determined for the various substrates analyzed, is shown.

| Chromogenic Substrates | Specific Activity |
|---|---|
| H-D-Pro-HHT-Arg-pNA | 0.046 ± 0.001 |
| H-D-Lys(CBO)-Pro-Arg-pNA | 0.076 ± 0.008 |
| Z-Phe-Arg-pNA | 0.116 ± 0.006 |
| H-D-Val-Leu-Arg-pNA | 0.025 ± 0.003 |
| H-D-Val-Leu-Lys-pNA | 0.034 ± 0.003 |
| Suc-Ala-Ala-Pro-Phe-pNA | N.A. |
| Meo-Suc-Ala-Ala-Pro-Val-pNA | N.A. |

N.A. = No Activity

Compounds that modulate a serine protease of the present invention are identified through screening for the acceleration, or more commonly, the inhibition of the proteolytic activity. Although in the present case chromogenic activity is monitored by an increase in absorbance, fluorogenic assays or other methods such as FRET to measure proteolytic activity as mentioned above, can be employed. Compounds are dissolved in an appropriate solvent, such as DMF, DMSO, methanol, and diluted in water to a range of concentrations usually not exceeding 100 uM and are typically tested, though not limited to, a concentration of 1000-fold the concentration of protease. The compounds are then mixed with the protein stock solution, prior to addition to the reaction mixture. Alternatively, the protein and compound solutions may be added independently to the reaction mixture, with the compound being added either prior to, or immediately after, the addition of the protease D-G protein.

During the course of these investigations a submission in Genbank was identified (Genbank accession number AF216312) which is similar but distinct from the sequence described herein. Although the exact significance of the discrepancy between the protease D-G cDNA and the AF216312 sequence is not fully understood at this time, it may be a result of alternative splicing near the initiator ATG, thereby generating distinct coding sequences and consequently distinct proteins. Below is a GAP alignment between the nucleic acid sequences of the protease D-G cDNA (SEQ.ID.NO.:1) described herein on top and in upper case, and the AF216312 sequence indicated below and in lower case.

The Genbank explanatory information is reproduced as follows:
LOCUS AF216312 2079 bp mRNA
DEFINITION *Homo sapiens* type II membrane serine protease mRNA, complete cds.
ACCESSION AF216312VERSION AF216312.1 GI:6911218
SOURCE human.
ORGANISM *Homo sapiens* Eukaryota; Metazoa; Chordata; Craniata; Vertebrata; Mammalia; Eutheria; Primates; Catarrhini; Hominidae; Homo.

REFERENCE 1 (bases 1 to 2079)
AUTHORS Smeekens, S. S., Lorimer, D. D., Wang, E., Hou, J. and Linnevers, C.
TITLE MT-SP2, a novel type II membrane serine protease expressed in trachea, colon, and small intestine: identification, cloning, and chromosomal localization
JOURNAL Unpublished
REFERENCE 2 (bases 1 to 2079)
AUTHORS Smeekens, S. S., Lorimer, D. D., Wang, E., Hou, J. and Linnevers, C.
TITLE Direct Submission
JOURNAL Submitted (14 Dec. 1999) Axys Pharmaceuticals, Inc, 180 Kimball Way, South San Francisco, Calif. 94080, USA

```
               SEQ.ID.NO.:1 x AF216312.Seq

51 CACTCCTGGAATACACAGAGAGAGGCAGCAGCTTGCTCAGCGGACAAGGA 100
                              ||||||||||| ||||||||||
      1 ................. gagaggcagcagcttgttcagcggacaagga 31
                    .         .         .         .         .
    101 TGCTGGGCGTGAGGGACCAAGGCCTGCCCTGCACTCGGGCCTCCTCCAGC 150
        ||||||||||||||||||||||||||||||
     32 tgctgggcgtgagggaccaaggcctgccctgcactcgggcctcctccagc 81
                    .         .         .         .         .
    151 CAGTGCTGACCAGGGACTTCTGACCTGCTGGCCAGCCAGGACCTGTGTGG 200
        ||||||||||||||||||||||||||||||
     82 cagtgctgaccagggacttctgacctgctggccagccaggacctgtgtgg 131
                    .         .         .         .         .
    201 GGAGGCCCTCCTGCTGCCTTGGGGTGACAATCTCAGCTCCAGGCTACAGG 250
        ||||||||||||||||||||||||||||||
    132 ggaggccctcctgctgccttggggtgacaatctcagctccaggctacagg 181
                    .         .         .         .         .
    251 GAGACCGGGAGGATCACAGAGCCAGCAT......GGATCCTGACAGTGAT 294
        ||||||||||||||||||          ||||||||||
    182 gagaccgggaggatcacagagccagcatggtacaggatcctgacagtgat 231
                    .         .         .         .         .
    295 CAACCTCTGAACAGCCTCGATGTCAAACCCCTGCGCACCCCGTATCCC    344
        ||||||||||||||||||||||||||||||
    232 caacctctgaacagcctcgatgtcaaacccctgcgcaaacccgtatccc  281
                    .         .         .         .         .
    345 CATGGAGACCTTCAGAAAG.GTGGGGATCCCCATCATCATAGCACTACTG 393
        |||||||||| ||||||||||||||||||
    282 catggagaccttcagaaagtgtggggatccccatcatcatagcactactg 331
                    .         .         .         .         .
```

-continued

SEQ.ID.NO.:1 × AF216312.Seq

```
394 AGCCTGGCGAGTATCATCATTGTGGTTGTCCTCATCAAGGTGATTCTGGA 443
    ||||||||||||||||||||||||||||||||||||||||||||||||||
332 agcctggcgagtatcatcattgtggttgtcctcatcaaggtgattctgga 381

444 TAAATACTACTTCCTCTGCGGGCAGCCTCTCCACTTCATCCCGAGGAAGC 493
    ||||||||||||||||||||||||||||||||||||||||||||||||||
382 taaatactacttcctctgcgggcagcctctccacttcatcccgaggaagc 431

494 AGCTGTGTGACGGAGAGCTGGACTGTCCCTTGGGGGAGGACGAGGAGCAC 543
    ||||||||||||||||||||||||||||||||||||||||||||||||||
432 agctgtgtgacggagagctggactgtcccttgggggaggacgaggagcac 481

544 TGTGTCAAGAGCTTCCCCGAAGGGCCTGCAGTGGCAGTCCGCCTCTCCAA 593
    ||||||||||||||||||||||||||||||||||||||||||||||||||
482 tgtgtcaagagcttccccgaagggcctgcagtggcagtccgcctctccaa 531

594 GGACCGATCCACACTGCAGGTGCTGGACTCGGCCACAGGGAACTGGTTCT 643
    ||||||||||||||||||||||||||||||||||||||||||||||||||
532 ggaccgatccacactgcaggtgctggactcggccacagggaactggttct 581

644 CTGCCTGTTTCGACAACTTCACAGAAGCTCTCGCTGAGACGCCTGTAGG  693
    ||||||||||||||||||||||||||||||||||||||||||||||||
582 ctgcctgtttcgacaacttcacagaagctctcgctgagacagcctgtagg 631

694 CAGATGGGCTACAGCAGCAAACCCACTTTCAGAGCTGTGGAGATTGGCCC 743
    ||||||||||||||||||||||||||||||||||||||||||||||||||
632 cagatgggctacagcagcaaacccactttcagagctgtggagattggccc 681

744 AGACCAGGATCTGGATGTTGTTGAAATCACAGAAAACAGCCAGGAGCTTC 793
    ||||||||||||||||||||||||||||||||||||||||||||||||||
682 agaccaggatctggatgttgttgaaatcacagaaaacagccaggagcttc 731

794 GCATGCGGAACTCAAGTGGGCCCTGTCTCTCAGGCTCCCTGGTCTCCCTG 843
    ||||||||||||||||||||||||||||||||||||||||||||||||||
732 gcatgcggaactcaagtgggccctgtctctcaggctccctggtctccctg 781

844 CACTGTCTTGCCTGTGGGAAGAGCCTGAAGACCCCCCGTGTGGTGGGTGG 893
    ||||||||||||||||||||||||||||||||||||||||||||||||||
```

-continued

| SEQ.ID.NO.:1 x AF216312.Seq |
|---|

```
 782 cactgtcttgcctgtgggaagagcctgaagacccccgtgtggtgggtgg  831
              .         .         .         .         .

894 GGAGGAGGCCTCTGTGGATTCTTGGCCTTGGCAGGTCAGCATCCAGTACG  943
     |||||||||||||||||||||||||||||||||||||||||||||||||
 832 ggaggaggcctctgtggattcttggccttggcaggtcagcatccagtacg  881
              .         .         .         .         .

944 ACAAACAGCACGTCTGTGGAGGGAGCATCCTGGACCCCCACTGGGTCCTC  993
     |||||||||||||||||||||||||||||||||||||||||||||||||
 882 acaaacagcacgtctgtggagggagcatcctggaccccactgggtcctc   931
              .         .         .         .         .

994 ACGGCAGCCCACTGCTTCAGGAAACATACCGATGTGTTCAACTGGAAGGT 1043
     |||||||||||||||||||||||||||||||||||||||||||||||||
 932 acggcagcccactgcttcaggaaacataccgatgtgttcaactggaaggt  981
              .         .         .         .         .

1044 GCGGGCAGGCTCAGACAAACTGGGCAGCTTCCCATCCCTGGCTGTGGCCA 1093
     |||||||||||||||||||||||||||||||||||||||||||||||||
 982 gcgggcaggctcagacaaactgggcagcttcccatccctggctgtggcca 1031
              .         .         .         .         .

1094 AGATCATCATCATTGAATTCAACCCCATGTACCCCAAAGACAATGACATC 1143
     |||||||||||||||||||||||||||||||||||||||||||||||||
1032 agatcatcatcattgaattcaaccccatgtaccccaaagacaatgacatc 1081
              .         .         .         .         .

1144 GCCCTCATGAAGCTGCAGTTCCCACTCACTTTCTCAGGCACAGTCAGGCC 1193
     |||||||||||||||||||||||||||||||||||||||||||||||||
1082 gccctcatgaagctgcagttcccactcactttctcaggcacagtcaggcc 1131
              .         .         .         .         .

1194 CATCTGTCTGCCCTTCTTTGATGAGGAGCTCACTCCAGCCACCCCACTCT 1243
     |||||||||||||||||||||||||||||||||||||||||||||||||
1132 catctgtctgcccttctttgatgaggagctcactccagccaccccactct 1181
              .         .         .         .         .

1244 GGATCATTGGATGGGCTTTACGAAGCAGAATGGAGGGAAGATGTCTGAC  1293
     |||||||||||||||||||||||||||||||||||||||||||||||||
1182 ggatcattggatgggctttacgaagcagaatggagggaagatgtctgac  1231
              .         .         .         .         .

1294 ATACTGCTGCAGGCGTCAGTCCAGGTCATTGACAGCACACGGTGCAATGC 1343
     |||||||||||||||||||||||||||||||||||||||||||||||||
1232 atactgctgcaggcgtcagtccaggtcattgacagcacacggtgcaatgc 1281
              .         .         .         .         .
```

-continued

| SEQ.ID.NO.:1 x AF216312.Seq |
|---|

```
1344 AGACGATGCGTACCTGGGGGAAGTCACCGAGAAGATGATGTGTGCAGGCA 1393
     |||||||||| |||||||||||||||||||||||||||||||
1282 agacgatgcgtaccaggggaagtcaccgagaagatgatgtgtgcaggca 1331

1394 TCCCGGAAGGGGGTGTGGACACCTGCCAGGGTGACAGTGGTGGGCCCCTG 1443
     ||||||||||||||||||||||||||||||||||||||||||||||||||
1332 tcccggaagggggtgtggacacctgccagggtgacagtggtgggcccctg 1381

1444 ATGTACCAATCTGACCAGTGGCATGTGGTGGGCATCGTTAGCTGGGGCTA 1493
     ||||||||||||||||||||||||||||||||||||||||||||||||||
1382 atgtaccaatctgaccagtggcatgtggtgggcatcgttagctggggcta 1431

1494 TGGCTGCGGGGGCCCGAGCACCCCAGGGGTATACACCAAGGTCTCAGCCT 1543
     ||||||||||||||||||||| ||||||||||||||||||||
1432 tggctgcgggggcccgagcaccccaggagtatacaccaaggtctcagcct 1481

1544 ATCTCAACTGGATCTACAATGTCTGGAAGGCTGAGCTGTAATGCTGCTGC 1593
     ||||||||||||||||||||||||||||||||||||||||||||||||||
1482 atctcaactggatctacaatgtctggaaggctgagctgtaatgctgctgc 1531

1594 CCCTTTGCAGTGCTGGGAGCCGCTTCCTTCCTGCCCTGCCCACCTGGGGA 1643
     ||||||||||||||||||||||||||||||||||||||||||||||||||
1532 ccctttgcagtgctgggagccgcttccttcctgccctgcccacctgggga 1581

1644 TCCCCCAAAGTCAGACACAGAGCAAGAGTCCCCTTGGGTACACCCCTCTG 1693
     ||||||||||||||||||||||||||||||||||||||||||||||||||
1582 tcccccaaagtcagacacagagcaagagtccccttgggtacacccctctg 1631

1694 CCCACAGCCTCAGCATTTCTTGGAGCAGCAAAGGGCCTCAATTCCTATAA 1743
     |||||||||||||||||||||||||||||||||||||||||||| |||
1632 cccacagcctcagcatttcttggagcagcaaagggcctcaattcctgtaa 1681

1744 GAGACCCTCGCAGCCCAGAGGCGCCCAGAGGAAGTCAGCAGCCCTAGCTC 1793
     ||||||||||||||||||||||||||||||||||||||||||||||||||
1682 gagaccctcgcagcccagaggcgcccagaggaagtcagcagccctagctc 1731

1794 GGCCACACTTGGTGCTCCCAGCATCCCAGGGAGAGACACAGCCCACTGAA 1843
     ||||||||||||||||||||||||||||||||||||||||||||||||||
```

-continued

| SEQ.ID.NO.:1 × AF216312.Seq |
|---|

```
1732 ggccacacttggtgctcccagcatcccagggagagacacagcccactgaa 1781
            .         .         .         .         .
1844 CAAGGTCTCAGGGGTATTGCTAAGCCAAGAAGGAACTTTCCCACACTACT 1893
     |||||||||||||||||||||||||||||||||||||||||||||||||
1782 caaggtctcaggggtattgctaagccaagaaggaactttcccacactact 1831
            .         .         .         .         .
1894 GAATGGAAGCAGGCTGTCTTGTAAAAGCCCAGATCACTGTGGGCTGGAGA 1943
     |||||||||||||||||||||||||||||||||||||||||||||||||
1832 gaatggaagcaggctgtcttgtaaaagcccagatcactgtgggctggaga 1881
            .         .         .         .         .
1944 GGAGAAGGAAAGGGTCTGCGCCAGCCCTGTCCGTCTTCACCCATCCCCAA 1993
     |||||||||||||||||||||||||||||||||||||||||||||||||
1882 ggagaaggaaagggtctgcgccagccctgtccgtcttcacccatccccaa 1931
            .         .         .         .         .
1994 GCCTACTAGAGCAAGAAACCAGTTGTAATATAAAATGCACTG.CCTACTG 2042
     ||||||||||||||||||||||||||||||||| |||||
1932 gcctactagagcaagaaccagttgtaatataaaatgcactgccctactg  1981
            .         .         .         .         .
2043 TTGGTATGACTACCGTTACCTACTGTTGTCATTGTTATTACAGCTATGGC 2092
     |||||||||||||||||||||||||||||||||||||||||||||||||
1982 ttggtatgactaccgttacctactgttgtcattgttattacagctatggc 2031
            .         .         .         .         .
2093 CACTATTATTAAAGAGCTGTGTAACATCA...................   2121
     |||||||||||||||||||||||||||||
2032 CACTATTATTAAAGAGCTGTGTAACATCAAAAAAAAAAAAAAAAAAAAA  2079
```

Below is a GAP alignment between the amino acid sequences of the protease D-G cDNA (SEQ.ID.NO.:2) described herein, on top with the predicted transmembrane domain in lower case, and that encoded by the AF216312 sequence indicated below.

| SEQ.ID.NO.:2 × AF216312.Pro |
|---|

```
            .         .         .         .         .
  1 MDPDSDQPLNSLDVKPLRKPRIPMETFRKVgipiiiallslasiiivvvl 50
                 |   |   |       |||||||||||||||||||
  1 ............MSNPCANPVSPWRPSESVGIPIIIALLSLASIIIVVVL 38
            .         .         .         .         .
```

-continued

SEQ.ID.NO.:2 × AF216312.Pro

```
 51 ikVILDKYYFLCGQPLHFIPRKQLCDGELDCPLGEDEEHCVKSFPEGPAV 100
    |||||||||||||||||||||||||||||||||||||||||||||||||
 39 IKVILDKYYFLCGQPLHFIPRKQLCDGELDCPLGEDEEHCVKSFPEGPAV  88

101 AVRLSKDRSTLQVLDSATGNWFSACFDNFTEALAETACRQMGYSSKPTFR 150
    |||||||||||||||||||||||||||||||||||||||||||||||||
 89 AVRLSKDRSTLQVLDSATGNWFSACFDNFTEALAETACRQMGYSSKPTFR 138

151 AVEIGPDQDLDVVEITENSQELRMRNSSGPCLSGSLVSLHCLACGKSLKT 200

139 AVEIGPDQDLDVVEITENSQELRMRNSSGPCLSGSLVSLHCLACGKSLKT 188

201 PRVVGGEEASVDSWPWQVSIQYDKQHVCGGSILDPHWVLTAAHCFRKHTD 250
    |||||||||||||||||||||||||||||||||||||||||||||||||
189 PRVVGGEEASVDSWPWQVSIQYDKQHVCGGSILDPHWVLTAAHCFRKHTD 238

251 VFNWKVRAGSDKLGSFPSLAVAKIIIIEFNPMYPKDNDIALMKLQFPLTF 300
    |||||||||||||||||||||||||||||||||||||||||||||||||
239 VFNWKVRAGSDKLGSFPSLAVAKIIIIEFNPMYPKDNDIALMKLQFPLTF 288

301 SGTVRPICLPFFDEELTPATPLWIIGWGFTKQNGGKMSDILLQASVQVID 350
    |||||||||||||||||||||||||||||||||||||||||||||||||
289 SGTVRPICLPFFDEELTPATPLWIIGWGFTKQNGGKMSDILLQASVQVID 338

351 STRCNADDAYQGEVTEKMMCAGIPEGGVDTCQGDSGGPLMYQSDQWHVVG 400
    |||||||||||||||||||||||||||||||||||||||||||||||||
339 STRCNADDAYQGEVTEKMMCAGIPEGGVDTCQGDSGGPLMYQSDQWHVVG 388

401 IVSWGYGCGGPSTPGVYTKVSAYLNWIYNVWKAEL 435
    ||||||||||||||||||||||||||||||||||
389 IVSWGYGCGGPSTPGVYTKVSAYLNWIYNVWKAEL 423
```

What is claimed is:

1. A protein in substantially pure form having protease D-G proteolytic activity, wherein the protein comprises the sequence set forth by SEQ ID NO: 2.

* * * * *

SEQUENCE LISTING

<160> NUMBER OF SEQ ID NOS: 9

<210> SEQ ID NO 1
<211> LENGTH: 2121
<212> TYPE: DNA
<213> ORGANISM: Homo sapiens

```
<400> SEQUENCE: 1
caacttcact tgtagggctg tttttaatcaa gctgcccaaa gtcccccaat cactcctgga        60
atacacagag agaggcagca gcttgctcag cggacaagga tgctgggcgt gagggaccaa       120
ggcctgccct gcactcgggc ctcctccagc cagtgctgac cagggacttc tgacctgctg       180
gccagccagg acctgtgtgg ggaggccctc ctgctgcctt ggggtgacaa tctcagctcc       240
aggctacagg gagaccggga ggatcacaga gccagcatgg atcctgacag tgatcaacct       300
ctgaacagcc tcgatgtcaa acccctgcgc aaaccccgta tccccatgga gaccttcaga       360
aagtggggga tccccatcat catagcacta ctgagcctgg cgagtatcat cattgtggtt       420
gtcctcatca aggtgattct ggataaatac tacttcctct gcgggcagcc tctccacttc       480
atcccgagga agcagctgtg tgacggagag ctggactgtc ccttggggga ggacgaggag       540
cactgtgtca agagcttccc cgaagggcct gcagtggcag tccgcctctc caaggaccga       600
tccacactgc agtgctggga ctcggccaca gggaactggt tctctgcctg tttcgacaac       660
ttcacagaag ctctcgctga cacagcctgt aggcagatgg gctacagcag caaacccact       720
ttcagagctg tggagattgg cccagaccag gatctggatg ttgttgaaat cacagaaaac       780
agccaggagc ttcgcatgcg gaactcaagt gggccctgtc tctcaggctc cctggtctcc       840
ctgcactgtc ttgcctgtgg gaagagcctg aagaccccc gtgtggtggg tggggaggag       900
gcctctgtgg attcttggcc ttggcaggtc agcatccagt acgacaaaca gcacgtctgt       960
ggagggagca tcctggaccc ccactgggtc tcacggcag cccactgctt caggaaacat      1020
accgatgtgt tcaactggaa ggtgcgggca ggctcagaca aactgggcag cttcccatcc      1080
ctggctgtgg ccaagatcat catcattgaa ttcaacccca tgtaccccaa agacaatgac      1140
atcgccctca tgaagctgca gttcccactc actttctcag gcacagtcag gcccatctgt      1200
ctgcccttct ttgatgagga gctcactcca gccaccccac tctggatcat tggatggggc      1260
tttacgaagc agaatggagg gaagatgtct gacatactgc tgcaggcgtc agtccaggtc      1320
attgacagca cacggtgcaa tgcagacgat gcgtacctgg gggaagtcac cgagaagatg      1380
atgtgtgcag gcatcccgga agggggtgtg gacacctgcc agggtgacag tggtgggccc      1440
ctgatgtacc aatctgacca gtggcatgtg gtgggcatcg ttagctgggg ctatggctgc      1500 ggggcccga gcaccccagg ggtatacacc aaggtctcag cctatctcaa ctggatctac      1560
aatgtctgga aggctgagct gtaatgctgc tgcccctttg cagtgctggg agccgcttcc      1620
ttcctgccct gcccacctgg ggatccccca agtcagaca cagagcaaga gtccccttgg      1680
gtacacccct ctgcccacag cctcagcatt tcttggagca gcaaagggcc tcaattccta      1740
taagagaccc tcgcagccca gaggcgccca gaggaagtca gcagcctag ctcggccaca      1800 cttggtgctc ccagcatccc agggagagac acagcccact gaacaaggtc tcagggtat      1860 tgctaagcca agaaggaact ttcccacact actgaatgga agcaggctgt cttgtaaaag      1920
cccagatcac tgtgggctgg agaggagaag gaaagggtct gcgccagccc tgtccgtctt      1980
cacccatccc caagcctact agagcaagaa ccagttgta atataaaatg cactgcctac      2040
tgttggtatg actaccgtta cctactgttg tcattgttat tacagctatg gccactatta      2100
ttaaagagct gtgtaacatc a                                                2121

<210> SEQ ID NO 2
<211> LENGTH: 435
<212> TYPE: PRT
<213> ORGANISM: Homo sapiens
```

<400> SEQUENCE: 2

```
Met Asp Pro Asp Ser Asp Gln Pro Leu Asn Ser Leu Asp Val Lys Pro
 1               5                  10                  15

Leu Arg Lys Pro Arg Ile Pro Met Glu Thr Phe Arg Lys Val Gly Ile
            20                  25                  30

Pro Ile Ile Ile Ala Leu Leu Ser Leu Ala Ser Ile Ile Ile Val Val
        35                  40                  45

Val Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
65                  70                  75                  80

Cys Pro Leu Gly Glu Asp Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190

Ala Cys Gly Lys Ser Leu Lys Thr Pro Arg Val Val Gly Gly Glu Glu
        195                 200                 205

Ala Ser Val Asp Ser Trp Pro Trp Gln Val Ser Ile Gln Tyr Asp Lys
    210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Glu Phe Asn Pro Met Tyr Pro Lys Asp Asn Asp
        275                 280                 285

Ile Ala Leu Met Lys Leu Gln Phe Pro Leu Thr Phe Ser Gly Thr Val
    290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

Arg Cys Asn Ala Asp Asp Ala Tyr Gln Gly Glu Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415
```

```
Tyr Thr Lys Val Ser Ala Tyr Leu Asn Trp Ile Tyr Asn Val Trp Lys
                420                 425                 430
Ala Glu Leu
        435

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 3
acagcctcag catttcttgg                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 4
tcttgctcta gtaggcttgg                                                     20

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Nested
      probe

<400> SEQUENCE: 5
ttggtgctcc cagcatccca gggagagaca cagcccactg                               40

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 6
atgctctaga tgtggattct tggccttggc                                          30

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 7
gatgtctaga cagctcagcc ttccagacat tg                                       32

<210> SEQ ID NO 8
<211> LENGTH: 1189
<212> TYPE: DNA
<213> ORGANISM: Artificial Sequence
<220> FEATURE:
<223> OTHER INFORMATION: Description of Artificial Sequence: Fusion gene
```

<400> SEQUENCE: 8

```
gaattcacca ccatggacag caaaggttcg tcgcagaaat cccgcctgct cctgctgctg    60
gtggtgtcaa atctactctt gtgccagggt gtggtctccg actacaagga cgacgacgac   120
gtggacgcgg ccgctcttgc tgcccccttt gatgatgatg acaagatcgt tgggggctat   180
gctctagatg tggattcttg gccttggcag gtcagcatcc agtacgacaa acagcacgtc   240
tgtgaggga gcatcctgga ccccactgg gtcctcacgg cagcccactg cttcaggaaa     300
cataccgatg tgttcaactg gaaggtgcgg gcaggctcag acaaactggg cagcttccca   360
tccctggctg tggccaagat catcatcatt gaattcaacc ccatgtaccc caaagacaat   420
gacatcgccc tcatgaagct gcagttccca ctcactttct caggcacagt caggcccatc   480
tgtctgccct tctttgatga ggagctcact ccagccaccc cactctggat cattggatgg   540
ggctttacga agcagaatgg agggaagatg tctgacatac tgctgcaggc gtcagtccag   600
gtcattgaca gcacacggtg caatgcagac gatgcgtacc tggggaagt caccgagaag    660
atgatgtgtg caggcatccc ggaagggggt gtggacacct gccagggtga cagtggtggg   720
cccctgatgt accaatctga ccagtggcat gtggtgggca tcgttagctg ggctatggc    780
tgcggggccc gagcaccccc aggggtatac accaaggtct cagcctatct caactggatc   840
tacaatgtct ggaaggctga gctgtctaga catcaccatc accatcacta gcggccgctt   900
ccctttagtg agggttaatg cttcgagcag acatgataag atacattgat gagtttggac   960
aaaccacaac tagaatgcag tgaaaaaaat gctttatttg tgaaatttgt gatgctattg  1020
ctttatttgt aaccattata agctgcaata acaagttag cttgtcgaga agtactagag   1080
gatcataatc agccatacca catttgtaga ggttttactt gctttaaaaa acctcccaca  1140
cctcccctg aacctgaaac ataaaatgaa tgcaattgtt gttgttaac                 1189
```

<210> SEQ ID NO 9
<211> LENGTH: 292
<212> TYPE: PRT
<213> ORGANISM: Artificial Sequence
<220> FEATURE:
<223> OTHER INFORMATION: Description of Artificial Sequence: Fusion gene

<400> SEQUENCE: 9

```
Met Asp Ser Lys Gly Ser Ser Gln Lys Ser Arg Leu Leu Leu Leu Leu
  1               5                  10                  15

Val Val Ser Asn Leu Leu Leu Cys Gln Gly Val Val Ser Asp Tyr Lys
                 20                  25                  30

Asp Asp Asp Asp Val Asp Ala Ala Ala Leu Ala Ala Pro Phe Asp Asp
             35                  40                  45

Asp Asp Lys Ile Val Gly Gly Tyr Ala Leu Asp Val Asp Ser Trp Pro
         50                  55                  60

Trp Gln Val Ser Ile Gln Tyr Asp Lys Gln His Val Cys Gly Gly Ser
 65                  70                  75                  80

Ile Leu Asp Pro His Trp Val Leu Thr Ala Ala His Cys Phe Arg Lys
                 85                  90                  95

His Thr Asp Val Phe Asn Trp Lys Val Arg Ala Gly Ser Asp Lys Leu
            100                 105                 110

Gly Ser Phe Pro Ser Leu Ala Val Ala Lys Ile Ile Ile Glu Phe
        115                 120                 125

Asn Pro Met Tyr Pro Lys Asp Asn Asp Ile Ala Leu Met Lys Leu Gln
    130                 135                 140
```

-continued

```
Phe Pro Leu Thr Phe Ser Gly Thr Val Arg Pro Ile Cys Leu Pro Phe
145                 150                 155                 160

Phe Asp Glu Glu Leu Thr Pro Ala Thr Pro Leu Trp Ile Ile Gly Trp
                165                 170                 175

Gly Phe Thr Lys Gln Asn Gly Gly Lys Met Ser Asp Ile Leu Leu Gln
                180                 185                 190

Ala Ser Val Gln Val Ile Asp Ser Thr Arg Cys Asn Ala Asp Asp Ala
                195                 200                 205

Tyr Gln Gly Glu Val Thr Glu Lys Met Met Cys Ala Gly Ile Pro Glu
                210                 215                 220

Gly Gly Val Asp Thr Cys Gln Gly Asp Ser Gly Gly Pro Leu Met Tyr
225                 230                 235                 240

Gln Ser Asp Gln Trp His Val Val Gly Ile Val Ser Trp Gly Tyr Gly
                245                 250                 255

Cys Gly Gly Pro Ser Thr Pro Gly Val Tyr Thr Lys Val Ser Ala Tyr
                260                 265                 270

Leu Asn Trp Ile Tyr Asn Val Trp Lys Ala Glu Leu Ser Arg His His
                275                 280                 285

His His His His
290
```